United States Patent
Wahl et al.

(10) Patent No.: US 12,178,510 B2
(45) Date of Patent: Dec. 31, 2024

(54) DETERMINING A VISUAL PERFORMANCE OF AN EYE OF A PERSON

(71) Applicant: Carl Zeiss Vision International GmbH, Aalen (DE)

(72) Inventors: Siegfried Wahl, Donzdorf (DE); Peter Essig, Karlsruhe (DE); Yannick Sauer, Tübingen (DE)

(73) Assignee: Carl Zeiss Vision International GmbH, Aalen (DE)

(*) Notice: Subject to any disclaimer, the term of this patent is extended or adjusted under 35 U.S.C. 154(b) by 0 days.

(21) Appl. No.: 18/642,291

(22) Filed: Apr. 22, 2024

(65) Prior Publication Data
US 2024/0268660 A1 Aug. 15, 2024

Related U.S. Application Data

(63) Continuation of application No. PCT/EP2022/086385, filed on Dec. 16, 2022.

(30) Foreign Application Priority Data

Dec. 17, 2021 (EP) ..................................... 21215619

(51) Int. Cl.
*A61B 3/103* (2006.01)
*A61B 3/00* (2006.01)
*A61B 3/113* (2006.01)

(52) U.S. Cl.
CPC ............ *A61B 3/103* (2013.01); *A61B 3/0025* (2013.01); *A61B 3/0091* (2013.01); *A61B 3/113* (2013.01)

(58) Field of Classification Search
CPC ..... A61B 3/103; A61B 3/0025; A61B 3/0091; A61B 3/113
(Continued)

(56) References Cited

U.S. PATENT DOCUMENTS 10,444,514 B2 * 10/2019 Abou Shousha ...... A61B 3/028
10,702,141 B2 * 7/2020 Mantysalo ............. A61B 5/163
(Continued)

FOREIGN PATENT DOCUMENTS

CN 105682537 A 6/2016
CN 111511318 A 8/2020
(Continued)

OTHER PUBLICATIONS

Howe et al., "The objective assessment of contrast sensitivity function by electrophysiological means," British Journal of Ophthalmology, vol. 68, No. 9, pp. 626 to 638, 1984.
(Continued)

*Primary Examiner* — Mohammed A Hasan
(74) *Attorney, Agent, or Firm* — Tautz & Schuhmacher LLC; Georg Hasselmann

(57) ABSTRACT

A computer-implemented method, a computer program, an apparatus, and a remote apparatus for determining at least one visual performance of at least one eye of a person for a plurality of points in a visual field of the person from tracking data by using at least the first spatial location of at least one visual fixation mark and the second spatial location of at least one visual stimulus are disclosed. An attention level of the person is determined by evaluating a time-related difference in reaction times between at least one particular measurement cycle and at least one subsequent measurement cycle. The automated visual performance test can be performed by any person irrespective of being an ophthalmologist or optometry specialist or not, particularly by using a mobile device.

13 Claims, 3 Drawing Sheets

(58) Field of Classification Search
USPC .......................................................... 351/209
See application file for complete search history.

(56) References Cited

U.S. PATENT DOCUMENTS

| | | | |
|---|---|---|---|
| 2007/0265507 A1* | 11/2007 | de Lemos | A61B 5/16 |
| | | | 600/300 |
| 2010/0195051 A1* | 8/2010 | Murray | A61B 3/024 |
| | | | 351/209 |
| 2013/0054576 A1* | 2/2013 | Karmarkar | G06F 16/95 |
| | | | 707/E17.014 |
| 2014/0192325 A1 | 7/2014 | Klin et al. | |
| 2015/0112224 A1* | 4/2015 | Super | A61B 3/02 |
| | | | 600/558 |
| 2016/0262613 A1 | 9/2016 | Klin et al. | |
| 2019/0150727 A1 | 5/2019 | Blaha et al. | |
| 2020/0305707 A1 | 10/2020 | Fink et al. | |
| 2021/0112226 A1 | 4/2021 | Abou Shousha | |
| 2022/0039645 A1 | 2/2022 | Leube et al. | |
| 2023/0143549 A1 | 5/2023 | Shimazaki et al. | |

FOREIGN PATENT DOCUMENTS

| | | |
|---|---|---|
| EP | 3730037 A1 | 10/2020 |
| GB | 2375821 A1 | 11/2002 |
| WO | 2021/200604 A1 | 10/2021 |

OTHER PUBLICATIONS

Rosen et al., "Quick contrast sensitivity measurements in the periphery," Journal of Vision, vol. 14, No. 8, pp. 1 to 10, 2014.
Bonneh et al., "Contrast sensitivity revealed by microsaccades," Journal of Vision, vol. 15, No. 9, pp. 1 to 11, 2015.
Mooney et al., "Curveball: A tool for rapid measurement of contrast sensitivity based on smooth eye movements," Journal of Vision, vol. 18, No. 12, pp. 1 to 7, 2018.
European Search Report issued in EP 21215619.4, to which this application claims priority, mailed May 16, 2022.
International Search Report and Written Opinion issued in PCT/EP2022/086385, to which this application claims priority, mailed Mar. 16, 2023.
International Preliminary Report on Patentability issued in PCT/EP2022/086385, to which this application claims priority, mailed Mar. 5, 2024.
Industrial Norm "Ophthalmic optics—Spectacle lenses—Vocabulary (ISO 13666:2019)," English version EN ISO 13666:2019, Dec. 2019.
Office Action by the European Patent Office (EPO) issued in EP 22 840 064.4, which is a counterpart hereof, mailed on Jun. 25, 2024.
Office Action by the Chinese Patent Office (CIPO) issued in CN202280077526.2, which is a counterpart hereof, mailed on Aug. 17, 2024 and English-language translation thereof.

* cited by examiner

DETERMINING A VISUAL PERFORMANCE OF AN EYE OF A PERSON

CROSS REFERENCE TO RELATED APPLICATIONS

This application is a continuation application of international patent application PCT/EP2022/086385, filed on Dec. 16, 2022 and designating the U.S., which claims priority to European patent application 21215619.4, filed on Dec. 17, 2021, both of which are hereby incorporated by reference in their entireties.

TECHNICAL FIELD

The present disclosure relates to a computer-implemented method, a computer program, an apparatus and a remote apparatus for determining at least one visual performance of at least one eye of a person.

BACKGROUND

Howe, J. W. and Mitchell, K. W., "The objective assessment of contrast sensitivity function by electrophysiological means," British Journal of Ophthalmology, 68(9), pp. 626 to 638, 1984, describes that in recent years it has been shown that it is of considerable clinical value to determine the visual contrast sensitivity function of the patient. They describe an approach which exploits electrophysiological techniques using the visual evoked cortical potential (VECP) to checkerboard onset-offset stimulation. Its application in a variety of disorders of the visual system is described. The importance of selecting the most appropriate stimulus parameters is discussed, and the relative advantages and disadvantages as compared with psychophysical methods are appraised.

Mooney, S. W., Hill, N. J., Tuzun, M. S., Alam, N. M., Carmel, J. B. and Prusky, G. T., "Curveball: A tool for rapid measurement of contrast sensitivity based on smooth eye movements," Journal of Vision, 18(12), 7-7, 2018 describes that the contrast sensitivity function (CSF) is an informative measure of visual function, but current tools for assessing it are limited by the attentional, motor, and communicative abilities of the participant. Impairments in these abilities can prevent participants from engaging with tasks or following an experimenter's instructions. They particularly describe an efficient new tool for measuring contrast sensitivity, Curveball, and empirically validate it with a sample of healthy adults. The Curveball algorithm continuously infers stimulus visibility through smooth eye tracking instead of perceptual report, and rapidly lowers stimulus contrast in real time until a threshold is found. The procedure requires minimal instruction to administer and takes only five minutes to estimate a full CSF, which is comparable to the best existing methods available for healthy adults. Task repeatability was high. They also present evidence that the task is robust across illumination changes, well correlated with results from conventional psychophysical methods, and highly sensitive to improvements in visual acuity from refractive correction. Their findings indicate that Curveball is a promising means of accurately assessing contrast sensitivity in previously neglected populations.

Bonnch, Y. S., Adini, Y., & Polat, U., "Contrast sensitivity revealed by microsaccades," Journal of Vision, 15(9), 11-11, 2015 describes that microsaccades are small rapid and involuntary eye movements that occur during fixation in an apparently stochastic manner. They are known to be inhibited in response to sensory transients, with a time course that depends on the stimulus parameters and attention. However, the time-related precision of their onsets and the degree to which they can be used to assess the response of the visual system to basic stimulus parameters is currently unknown. In the publication they studied microsaccade response properties as a function of the contrast and spatial frequency of visual onsets. Observers viewed and silently counted 2-min sequences of Gabor patches presented briefly (100 ms) at 1 Hz. Contrast and spatial frequency were randomized in different experiments. They found that the microsaccade response time, as measured by the latency of the first microsaccade relative to stimulus onset following its release from inhibition, was sensitive to the contrast and spatial frequency of the stimulus and could be used to extract a contrast response function without the observers' response. They also found that contrast detection thresholds, measured behaviorally for different spatial frequencies, were highly and positively correlated with the microsaccade response time measured at high contrast (>4 times the threshold).

Robert Rosén et. al., "Quick contrast sensitivity measurements in the periphery," Journal of Vision, 14(8):3, 1-10, 2014 describes that measuring the CSF in the periphery of the eye is complicated. The lengthy measurement time precludes all but the most determined subjects. The aim of this study was to implement and evaluate a faster routine based on the quick CSF method (qCSF) but adapted to work in the periphery. Additionally, normative data is presented on neurally limited peripheral CSFs. A peripheral qCSF measurement using 100 trials can be performed in 3 min. The precision and accuracy were tested for three subjects under different conditions (number of trials, peripheral angles, and optical corrections). In the second part of the study, they collected three CSFs of 100 trials for six persons in the 20š nasal, temporal, inferior, and superior visual fields. The measurements were performed in an adaptive optics system running in a continuous closed loop. Contrast sensitivity was higher in the horizontal fields, and the inferior field was better than the superior. This modified qCSF method decreases the measurement time significantly and allows otherwise unfeasible studies of the peripheral CSF.

EP 3 730 037 A1 discloses a method, a device, and a computer program for determining a refractive error of an eye of a user, and a method of for manufacturing a spectacle lens for the eye of the user. The method for determining a refractive error of an eye of a user comprises the following steps: a) displaying a feature on a screen, wherein a parameter of the feature displayed on the screen is varied; b) acquiring an eye movement metric of the eye of the user as a function of the feature displayed on the screen; c) determining a time at which the eye movement metric of the eye of the user is used to determine a detection threshold of the refractive error of the eye of the user; d) determining a value for the refractive error of the eye of the user from the parameter determined at the time. A visual fixation mark is not displayed.

U.S. 2020/0305707A1 discloses an apparatus, software and methods for assessing ocular, ophthalmic, neurological, physiological, psychological and/or behavioral conditions. As disclosed herein, the conditions are assessed using eye-tracking technology that beneficially eliminates the need for a subject to fixate and maintain focus during testing or to produce a secondary (non-optical) physical movement or audible response, i.e., feedback. The subject is only required to look at a series of individual visual stimuli, which is generally an involuntary reaction. The reduced need for cognitive and/or physical involvement of a subject allows the present modalities to achieve greater accuracy, due to reduced human error, and to be used with a wide variety of subjects, including small children, patients with physical disabilities or injuries, patients with diminished mental capacity, elderly patients, animals, etc. A visual fixation mark is not displayed.

GB 2 375 821 A discloses a visual acuity testing system that includes a computer with a high-resolution display linked to a video camera. Vertical gratings of varying width are presented either side of a central target image or video, coincident with an iso-luminant image opposite the grating. A digital video camera adjacent to the display is employed to track eye position using software algorithms that relate eye movement to the position of the vertical grating. Software analysis adjusts for head movement, blinks and corneal reflexes. The system eliminates the need to lift acuity cards manually, and provides an automated and objective method of vision assessment in pre-verbal children and those unable to communicate in standard visual acuity tests. The appearance of the vertical grating is not time-varying.

U.S. Pat. No. 10,702,141 B2 discloses a perimeter or a campimeter with a visible fixation point and a method used in them. The method comprises at least the following steps: producing a fixation point having a first visual appearance to be shown to a patient; producing a stimulus shown to the patient at a stimulus time-point at a pre-defined location; activating a response device by the patient upon noticing the stimulus at a response time-point; and changing the fixation point to have a second visual appearance for a fixation point second visual appearance time interval near the stimulus time-point.

U.S. 2021/0112226 A1 discloses that, in certain embodiments, vision defect information may be generated via a dynamic eye-characteristic-based fixation point. In some embodiments, a first stimulus may be displayed at a first location on a user interface based on a fixation point for a visual test presentation. The fixation point for the visual test presentation may be adjusted during the visual test presentation based on eye characteristic information related to a user. As an example, the eye characteristic information may indicate a characteristic of an eye of the user that occurred during the visual test presentation. A second stimulus may be displayed during the visual test presentation at a second interface location on the user interface based on the adjusted fixation point for the visual test presentation. Vision defect information associated with the user may be generated based on feedback information indicating feedback related to the first stimulus and feedback related to the second stimulus.

U.S. 2019/0150727 A1 discloses methods and systems for assessing a visual field of a person. Information can be presented to a person undergoing a visual field testing in a manner that utilizes the person's natural tendency to look at an object that is displayed so that it attracts the person's attention. A fixation target can be displayed on a display viewed by a user. Once it is determined that the user has viewed the fixation target and the person's eye(s) location is determined, a test target is displayed on the display in a location corresponding to a location on the user's visual field. The test target is determined to be either detected or missed based on user input acquired as the user is viewing the display.

U.S. 10,444,514 B2 discloses that, in certain embodiments, enhancement of a field of view of a user may be facilitated via one or more dynamic display portions. In some embodiments, one or more changes related to one or more eyes of a user may be monitored. Based on the monitoring, one or more positions of one or more transparent display portions of a screen of wearable device may be adjusted, where the transparent display portions enable the user to see through the screen of the wearable device. A live video stream representing an environment of the user may be obtained via the wearable device. An enhanced video stream derived from the live video stream may be displayed on one or more other display portions of the screen of the wearable device.

SUMMARY

It is therefore an object of the present disclosure to provide to a computer-implemented method, a computer program, an apparatus, and a remote apparatus for determining at least one visual performance of at least one eye of a person, which at least partially overcome the problems of the related art.

It is a particular objective of the present disclosure to provide a reliable and efficient approach to examine a complex visual performance of a patient's peripheral field of view in an automatic examination process for a plurality of defined points in a visual field area. It is further object of the disclosure to monitor a time dependency of the visual field.

This problem is solved by a method, a computer-implemented method, a computer program, an apparatus, and a remote apparatus for determining at least one visual performance of at least one eye of a person wherein an attention level of the person is determined by evaluating a time-related difference in reaction times between at least one particular measurement cycle and at least one subsequent measurement cycle. Exemplary embodiments, which can be implemented in an isolated fashion or in any arbitrary combination, are discussed throughout the following description.

In a first aspect, the present disclosure relates to a computer-implemented method for determining at least one visual performance of at least one eye of a person, wherein the method comprises at least the following steps:

a) displaying on a screen to the at least one eye of a person at least one visual fixation mark configured to attract a visual perception of the person by directing a line of sight of the at least one eye of the person towards the visual fixation mark;

b) subsequently displaying on a screen to the at least one eye of the person at least one visual stimulus configured to elicit at least one eye movement in the at least one eye of the person towards the at least one visual stimulus;

c) generating tracking data about the at least one eye movement of the at least one eye of the person by using at least one eye-tracking device; and d) determining the at least one visual performance from the tracking data by using at least one processing device;

wherein the at least one visual performance of the at least one eye of the person is determined for at least one point in a visual field of the person by using a first spatial location of the at least one visual fixation mark and a second spatial location of the at least one visual stimulus; wherein an attention level of the person is determined by evaluating a time-related difference in the reaction times between the at least one particular measurement cycle and the at least one subsequent measurement cycle.

As generally used, the term "computer-implemented method" refers to a method which involves a programmable apparatus, in particular, a computer, a computer network, a processing device, such as comprised by a mobile communication device, or a readable medium carrying a program, whereby at least one of the steps of the method, specifically at least one of steps a), b), c) and/or d), are performed by using at least one computer program. Alternatively, the at least one computer program may be accessible by an apparatus which may be adapted for performing the method via a network, such as via an in-house network or via internet. With particular regard to the present disclosure, the present method can, thus, be performed on a programmable apparatus, which is configured for this purpose, such as by providing a computer program which is configured for such a purpose.

As generally used, the term "determine" or any grammatical variation thereof refers to a process of generating representative results which are, typically, denoted as "data". With particular regard to the present disclosure, the data comprise information, which are related to the at least one visual performance within a visual field of at least one eye of a person.

As further used herein, the term "visual performance" refers to a property at least indirectly and/or directly related to a performance of the at least one eye of the person which can be determined by investigating the at least one eye of the person by an adapted measurement procedure.

According to step a), to at least one eye of a person at least one visual fixation mark configured to attract a visual perception of the person by directing a line of sight of the at least one eye of the person towards the visual fixation mark is displayed on a screen. The at least one visual fixation mark may be presented visually to the at least one eye of the person, particularly in a perceivable manner.

As generally used, the term "displaying" or any grammatical deviation thereof refers to a presentation of at least one of an image, an item, text, or a video, particularly at least one of a visual fixation mark or a visual stimulus, on the at least one screen.

As generally used, the term "screen" refers to an electronic visual display device designated for the presentation of at least one of an image, an item, text, or a video transmitted electronically. With particular regard to the present disclosure, the screen may be configured for displaying the at least one visual fixation mark to the at least one eye of a person, particularly in such manner that the at least one visual fixation mark may be perceptible by the at least one eye of the person. The at least one visual fixation mark may also be displayed to be perceptible by both eyes of the person.

As used herein, the term "visual fixation mark" refers to an item configured to attract a visual perception of the person by directing a line of sight of the at least one eye of the person towards the visual fixation mark. The person is, particularly, attracted to fixate the visual fixation mark in such a manner that a line of sight of the at least one eye of the person intersects with the visual fixation mark for at least a predetermined time interval. Based on standard ISO 13666:2019, Section 3.2.24, the term "line of sight" refers to an path from a point of interest, i.e. a point of fixation, in object space to a center of an entrance pupil of the eye of the person and, further, comprise a continuation in image space from a center of an exit pupil to a retinal point of fixation, generally the foveola, in the eye of the person.

According to step b), subsequently to the at least one eye of the person at least one visual stimulus configured to elicit at least one eye movement in the at least one eye of the person towards the at least one visual stimulus is displayed on the screen. The at least one visual stimulus may be presented in a manner that it is perceptible by the at least one eye of the person. This may elicit the at least one eye movement. An eye movement elicited by the at least one visual stimulus may be an eye movement according to which the line of sight and/or the gaze position of the at least one eye of the person is directed towards the at least one visual stimulus. The at least one visual fixation mark may be presented on a first sub-screen and the at least one visual stimulus may be presented on at least one second sub-screen.

As used herein, the term "visual stimulus" refers to a graphical presentation of an item, which is known or reasonably to be expected by the person skilled in the art to elicit the at least one desired type of eye movements in the at least one eye of the person. The at least one visual stimulus may be displayed at a spatial location on the screen that is different from the spatial location on the screen of the at least one fixation mark.

As generally used, the term "eliciting" or any grammatical deviation thereof refers to purpose of the displayed item, particularly the at least one visual stimulus and/or at least one fixation mark, namely the purpose to induce at least one eye movement of the person. The term "eye movement" refers to a time-variance of the line of sight and/or the gaze position of the at least one eye. The at least one eye movement that may be relevant for the present disclosure, is the eye movement from the at least one visual fixation mark to the at least one visual stimulus, or vice versa. This eye movement causes the line of sight of the at least one eye of the person to change from intersecting the at least one visual fixation mark to intersecting the at least one visual stimulus, or vice versa.

A sequence of step a) and b) causes the at least one eye of the person to i) fixate the at least one visual fixation target and then ii) fixate the at least one visual stimulus. A further sequence of step a) and b) causes the at least one eye of the person to iii) fixate the at least one visual fixation target again and then ii) fixate the at least one visual stimulus again. This eye movement may be induced by a different spatial location of the at least one visual fixation mark and the at least one visual stimulus.

According to step c), tracking data about the at least one eye movement of the at least one eye of the person by using at least one eye-tracking device is generated, particularly tracking data about the at least one eye movement of the at least one eye of the person moving towards the at least one visual stimulus by using at least one eye-tracking device is generated.

As generally used, the term "tracking" or any grammatical deviation thereof refers to recording motions of the at least one eye by using the at least one eye-tracking device. As generally used, the term "eye-tracking device" refers to a device that is used to record the motion of the at least one eye of the person, particularly a change of the line of sight and/or a gaze position of the at least one eye of the person. As a result of the recording, eye tracking data comprising information about the motion of the at least one eye of the person is generated, wherein the information about the motion of the at least one eye of the person may be given by the time-variance of the line of sight and/or the gaze position of the at least one eye. At least one outcome may be provided comprising the tracking data.

According to step d), the at least one visual performance from the tracking data is determined by using at least one processing device. The term "processing device" refers to at least one and/or a plurality of components of a computer system designated to process data, particularly process input data to generate output data. The tracking data may be considered as input data.

In accordance with the present disclosure, the at least one visual performance of the at least one eye of the person is determined for at least one point, typically a plurality of points, in the visual field of the person by further using at least a first spatial location of the at least one visual fixation mark and a second spatial location of the at least one visual stimulus during step d). As generally used, the term "visual field" refers to a spatial area which is perceptible by the at least one eye of the person. The second spatial location of the at least one visual stimulus on the screen may be assigned to a particular point in the visual field using an assignment rule. As generally used, the term "assignment rule" refers to a relationship between two parameters, especially between the second spatial location of the at least one visual stimulus on the screen and the particular point in the visual field.

Further in accordance with the present disclosure, an attention level of the person is determined by evaluating a time-related difference in the reaction times between the at least one particular measurement cycle and the at least one subsequent measurement cycle. As used herein, the term "time-related difference" refers to a value of a deviation between the reaction time recorded in the particular measurement cycle and the reaction time recorded in the subsequent measurement cycle. The term "subsequent measurement cycle", refers to a measurement cycle, which is performed at a point in time that is later than the point in time at which the particular measurement cycle was performed. As used herein, the term "attention level" refers to a score of the awareness of the person, particularly the degree of awareness to perceive a visual stimulus. A visual stimulus may be considered as perceived when to person is aware of a presence of the visual stimulus. It is not necessary to identify a visual stimulus for being aware of it.

The attention level may be determined spatially resolved, particularly in the visual field of the person. The attention level may be determined spatially resolved for a plurality of different points in the visual field of the person. Particularly therefore, the at least one time-related difference in the reaction times may be determined for at least one specific point. Alternatively, a plurality of time-related difference may be determined for a plurality of different points in the visual field of the person. Thereby, a map of the visual field may be generated, wherein the map comprises a plurality of time-related differences in reaction times, wherein each time-related difference in reaction times is related to a different point in the field of view. A size of the at least one visual stimulus being during any measurement cycle may remain.

In an exemplary embodiment, the at least one visual performance may be determined for a particular point in the visual field by assigning a particular spatial location to the particular point using an assignment rule. In an exemplary embodiment, the assignment rule considers the second spatial location of the at least one visual stimulus and the first spatial location of the at least one visual fixation mark; and particularly further considers a distance between the at least one eye of the person and the at least one visual stimulus and/or the at least one visual fixation mark.

In an exemplary embodiment, the first spatial location of the at least one visual fixation mark may be recorded during step a) and the second spatial location of the at least one visual stimulus may be recorded during step b). As used herein, the term "spatial location" refers to a specific position of the at least one respective item on the screen. As further used herein, the terms "first" and "second" are designed to distinguish the same kind of parameters, however, related to two different items. The item may be the at least one visual fixation mark and/or the at least one visual stimulus. In particular, the spatial location of an item may be recorded by using a signal which is configured for displaying the item on the at least one screen. As further used herein, the term "recording" or any grammatical variation thereof refers to producing data comprising information about the spatial location of the least one respective item and making the data available to the method.

The first spatial location of the at least one visual fixation mark may be recorded during step a). Further, the distance between the at least one eye of the person and the at least one visual stimulus and/or the at least one visual fixation mark may be recorded using a distance measuring device.

In an exemplary embodiment, a measurement cycle may comprise at least step b) and step c), more particular the measurement cycle may, additionally, comprise step a) and/or step d), wherein at least two measurement cycles, typically a plurality of measurement cycles, may be performed for determining a plurality of points in the visual field, specifically with a differing second spatial location of the at least one visual stimulus. In particular, the differing second spatial locations may have different eccentricity levels and/or a spatial orientations with regard to the at least one visual fixation mark. As used herein, the term "eccentricity level" refers to an absolute value of the vector connecting the at least one visual stimulus and the at least one fixation mark. The term "spatial orientation" refers to the direction of a vector connecting the second spatial location of the at least one visual stimulus and the first spatial location of the at least one fixation mark. As used herein, the term "plurality" refers to a quantity of at least two items.

In an exemplary embodiment, assigning the particular point in the visual field to the particular spatial location may be performed using an assignment rule, wherein the assignment rule may be maintained during the at least two measurement cycles and/or in all measurement cycles. The term "measurement cycle" refers herein to a sequence of at least the steps b) and c), wherein step a) and/or step d) may, additionally, be comprised by the measurement cycle. In an exemplary embodiment, at least one of: 2; 3; 4; 5; 7; 10; 15; 20; 25; 50; 75 or 100 cycles may be performed.

In an exemplary embodiment, the at least one visual fixation mark may be displayed in a center area of the screen, particularly directing the at least one eye of the person in a neutral position. The neutral position may be the primary position of the eye. In the primary position, the eye is looking straight ahead with a visual axis parallel to a sagittal plane of the head of the person.

In an exemplary embodiment, the center area may be completely enclosed by a surrounding area, wherein the at least one visual stimulus is displayed in the surrounding area in step b). As generally used, the term "completely enclosed" refers to the fact that the center area is delimited around its entire perimeter by the surrounding area.

In an exemplary embodiment, an angle $\alpha$ may be given between a first connecting line and a second connecting line, wherein the first connecting line connects a center of the at least one visual fixation mark and at least one reference position in the at least one eye of the person, wherein the second connecting line connects a center of the at least one visual stimulus and the at least one reference position in the at least one eye of the person, wherein $\alpha$ is larger than at least one of: 2°, 3°, 4°, 5°, 6°, 7°, or 8°. Thereby, the at least one visual stimulus is perceivable to the at least one eye of the person in a peripheral field of view when the at least one eye is fixating the visual fixation mark. As generally used, the term "field of view" refers to the extent of the observable world that is seen be the at least one eye of the person.

In an exemplary embodiment, the at least one reference position in the at least one eye of the person may be selected from at least one of:
 a pupil center;
 a corneal reflex; or
 a corneal apex.

As generally used, the term "corneal reflex" refers to a visible reflex on the cornea as generated by a light beam impinging on the eye. As further generally used, the term "corneal apex" refers to a most anterior point of a cornea when the at least one eye is in the primary position.

In an exemplary embodiment, the at least one visual stimulus can be display in any spatial orientation with regard to the at least one visual fixation mark. The term "spatial orientation" refers to the direction of a vector connecting the at least one visual stimulus and the at least one fixation mark.

In an exemplary embodiment, the surrounding area may correspond to the peripheral field of view, when the line of sight of the at least one eye of the person intersects with the at least one visual fixation mark. The term "peripheral field of view" is a portion of the field of view that comprises a vision occurring outside the gaze position. The line of sight is not comprised in the peripheral field of view. The peripheral field of view is outside of a central field of view.

In an exemplary embodiment, a third connecting line connecting an outer perimeter of the central field of view, particularly connecting a maximal circumference of the central field of view, and a reference position in the at least one eye of the person may be given, wherein a central field of view angle α between the third connecting line and the line of sight of the at least one eye of the person that intersects the reference position in the at least one eye of the person, is at least one of: 2°, 3°; 4°; 5°; 6°; 7° or 8°. The term "central field of view" refers to a portion of the field of view comprising the line of sight. The central field of view is surrounded by the peripheral field of view, particularly directly surrounded.

In an exemplary embodiment, the at least one visual performance of the at least one eye may be selected from at least one of:
 a contrast sensitivity;
 a visual acuity;
 a color vision;
 a time-related sensitivity; or
 a visual attention.

As generally used, the term "contrast sensitivity" refers to a property of at least one eye of a person to discern between different luminance levels in at least one visual target. As further generally used, the term "visual acuity" refers to a spatial resolution ability of the at least one eye of the person with respect to a structure within at least one visual target. As further generally used, the term "color vision" refers to a property of the at least one eye of the person to discern between different colors comprised by at least one visual target. As generally used, the term "time-related sensitivity" refers to the ability of the person to perceive a visual stimulus dependent on the time varying appearance of the at least one visual stimulus. As used herein, the term "visual attention" refers to a degree of awareness of the person, particularly a degree of awareness to perceive a visual stimulus. The visual attention may be analyzed to determine a time-variance of the ability of the person to concentrate, particularly the ability of the person to concentrate on visual input, specifically the ability of the person to concentrate dependent on the visual field of the person.

In an exemplary embodiment, the at least one eye movement may be a reflexive saccade in the at least one eye of the person. As generally used, the term "saccade" refers to a movement of the at least one eye of the person. Particularly a movement from the at least one fixation target to the at least one visual stimulus, or vice versa. The term "reflexive" refers to the fact that the person does not intend the eye movement. A reflexive saccade may be triggered by at least one of: an appearing of the at least one visual stimulus, a disappearing of the at least one a visual fixation mark, an appearing of the at least one a visual fixation mark, or a disappearing of the at least one a visual stimulus.

In an exemplary embodiment, a pupil size of the at least one eye of the person may, further, be recorded, particularly a time-variance of the pupil size of the at least one eye of the person. As generally used, the term "pupil" refers to a black hole having the recorded size located in a center of an iris of the at least one eye of the person. By recording the pupil size, pupil size data may be generated comprising information about the pupil size, particularly information about an area, a diameter, or a radius of the pupil.

In an exemplary embodiment, the at least one visual stimulus may be continuously displayed during step b). As used herein, the term "continuously" expresses that at least one visual stimulus is constantly displayed. The at least one visual stimulus is therefore not disappearing and appearing again during step b).

In an exemplary embodiment, the at least one visual stimulus may be selected from at least one of:
 at least one of an artificial pattern;
 a specific natural image; or
 a specific virtual image;
specifically,
 a grating, particularly a Gabor patch;
 a noise patch having at least one defined spatial frequency.

As used herein, the term "artificial pattern", as used herein, relates to a computer-generated pattern or to a pattern generated by a computer. The term "natural image" refers to a picture having been captured from a scene occurring in nature. By way of example, the natural image may be a picture of a landscape or of an interior scene, such as of a room or a part thereof. The term "virtual image" refers to a scene that was generated by using a computer program, typically, in a fashion that it may resemble and/or reconstruct a naturally occurring scene. As further generally used, the term "grating" refers to a regularly spaced collection of identical, parallel, elongated elements. The term "Gabor patches" refers to sinusoidal gratings, usually with a Gaussian envelope, which are known to be particularly useful as visual stimulus for the user's eye. As generally used, the term "noise" refers to an interference quantity with a broad non-specific frequency spectrum. The noise patch is the visual presentation of this noise with the further requirement that the noise patch has at least one defined spatial frequency. As further generally used, the term "spatial frequency" refers to a reciprocal value of a spatial distance reflecting a spatial period of repetition in the at least one visual stimulus. The grating, the Gabor patch and/or the noise patch may specifically be artificial patterns.

In an exemplary embodiment, an appearance of the at least one visual stimulus may be displayed in a time-varying manner on the at least one screen. As used herein, the term "appearance" refers to a look of the respective item, particularly the at least one visual stimulus and/or the at least one fixation mark. As used herein, the term "time-varying manner" refers to the fact that the appearance changes over time. Meaning that the appearance of the at least one visual stimulus is different at a first time from an appearance of the at least one visual stimulus at a second time. During time-varying the appearance, the at least one visual stimulus may be continuously displayed on the screen to the at least one eye of the person. The time-varying in the appearance of the at least one visual stimulus during step b) may thus be always perceivable by the at least one eye of the person.

In an exemplary embodiment, an appearance of the at least one visual fixation mark on the at least one screen and the appearance of the at least one visual stimulus on the at least one screen may differ from each other. As the appearance of the at least one visual stimulus and the at least one fixation mark is different, the person may by visually inspecting these items tell which item the person is perceiving. The appearance may not to be confused with a spatial location.

In an exemplary embodiment, the at least one visual fixation mark may be maintained in a constant manner during at least one measurement cycle, typically a plurality of measurement cycles. As used herein, the term "constant" implies that the appearance and/or the first spatial location of the at least one visual fixation mark on the screen is not time-varying. In other words, the appearance and/or the first spatial location of the at least one visual fixation mark may, as particularly typical, remain unchanged during it is displayed on the at least one screen, particularly during step a).

In an exemplary embodiment, at least one parameter attributed to the appearance of the at least one visual stimulus may be varied between a first value and a second value, particularly in a continuous manner, more particularly in a monotonous manner. As used herein, the term "varied" refers to a change in the appearance or a look of the at least one stimulus caused by a time-variance of one parameter attributed to the at least one visual stimulus. As used herein, the term "continuously" means that the parameter attributed to the appearance is varied perpetual and/or ongoing. The term "monotonously" means that the parameter attributed to the appearance is varied uniformly and/or in a steady manner. In other word, the change in the parameter may be not time-varying but be maintained.

In an exemplary embodiment, the at least one parameter may be selected from at least one of:
  a contrast, in particular for determining the contrast sensitivity;
  a spatial frequency, in particular for determining the visual acuity;
  a color, in particular for determining the color vision; or
  a time-related frequency, in particular for determining a time-related sensitivity.

As generally used, the term "contrast" refers to a luminance level in the at least one visual stimulus. As further generally used, the term "spatial frequency" refers to a reciprocal value of a spatial distance reflecting a spatial period of repetition in the at least one visual stimulus. As further generally used, the term "color" refers to a wavelength of a pattern as used in the at least one visual stimulus. As further generally used, the term "time-related frequency" refers to a repetition frequency of a periodic visual stimulus, particularly a number of repetitions of a periodic stimulus moving through a certain spatial point per unit time.

In an exemplary embodiment, for the at least one parameter attributed to the appearance at least one of:
  a first threshold may be determined at which the at least one eye movement in the at least one eye of the person is tracked for the first time; or
  a second threshold value may be determined at which the at least one eye movement in the at least one eye of the person is tracked for the last time.

As used herein, the term "threshold" refers to a minimum and/or maximum parameter setting that a stimulus must reach in order to trigger an excitation, a sensation or a reaction, particularly in order the elicit the at least on eye movement.

In an exemplary embodiment, a plurality of at least one parameter may be attributed to the appearance, particularly wherein a plurality of at least one parameter attributed to the appearance is varied between a first value and a second value, particularly in a continuous manner, more particularly in a monotonous manner.

In an exemplary embodiment, step c) may be performed during step a) and/or step b). In an exemplary embodiment, displaying of the at least one visual fixation mark is stopped before step b). As used herein, the term "stopped" refers to a cessation of the displaying of the at least one visual fixation. The at least one visual fixation mark is disappearing. The at least one visual fixation mark is then no longer perceivable to the at least one eye of the person.

In an exemplary embodiment, a gaze position of the at least one eye of the person may be checked during step a). As used herein, the term "gaze position" refers to a point of fixation in which the at least one line of sight and at least one object intersect. Particularly when the gaze position is known, it is possible that in an exemplary embodiment, the center of the fixation mark may be displayed in a central field of view during step a). In a further exemplary embodiment, the gaze position may be checked whether it is inside or outside an area of the at least one visual fixation mark during step a); particularly step b) may only be performed when the gaze position is inside the area of the at least one visual fixation mark.

In an exemplary embodiment, the area of the at least one visual fixation mark may at least partially and/or completely be located within the central field of view. The term "area of the at least one visual fixation mark" may refer to the field on the screen on which the item, particularly the at least one visual fixation mark, is displayed. In an exemplary embodiment, the at least one visual performance of the at least one eye may be determined outside the central field of view in a peripheral field of view. In an exemplary embodiment, the center and/or the area of the at least one visual stimulus may be displayed in the peripheral field of view during step b).

In an exemplary embodiment, displaying the at least one visual stimulus during step b) may be s stopped when the at least one eye movement has been tracked, in particular when the at least one eye movement has been elicited by the at least one visual stimulus. In an exemplary embodiment, during step b) the at least one visual stimulus may be displayed for a maximum of a predetermined time. As used herein, the term "predetermined time" refers to a defined time value.

In an exemplary embodiment, step b) may be repeated when at least one visual disturbance which affects the ability of the at least one eye of a person to observe the visual stimulus is detected. As used herein, the term "visual disturbance" refers to a reason and/or obstacle that hinders the at least one eye of the person to perceive the at least one visual stimulus and/or the at least one fixation mark. The visual impairment may particularly be at least indirectly and/or directly related to a condition of the at least one eye of the person. The visual impairment may be detectable by the at least one eye tracking device.

In an exemplary embodiment, the at least one visual disturbance may be selected from at least one of:
- a blink of the at least one eye of the person;
- a gaze position of the at least one eye of the person outside of the screen displaying the visual stimulus;
- a vergence angle between both eyes of the person showing that the person is not focusing on the screen; or
- a pupil size showing that the person is not focusing on the screen.

As generally used, the term "blink" refers to a rapid, usually involuntary and unnoticed closing and opening of an eyelid of the at least one eye of the person. As generally used, the term "vergence" refers to the simultaneous movement of both eyes of the person in opposite directions to obtain focus on a common gaze position. As generally used, the term "vergence angle" refers to an angle between the line of sights of both eyes that intersect in the gaze position.

In an exemplary embodiment, during step b) the second spatial location of the at least one visual stimulus may be maintained. In other words, the second spatial location of the at least one visual stimulus may not vary over time. In an exemplary embodiment, the second spatial location at which the at least one visual stimulus is displayed may be determined randomly by an algorithm. As used herein, the term "algorithm" refers to a set of instructions for solving a problem or a class of problems. The algorithm may, in particular, comprise instructions for a computer.

In an exemplary embodiment, the second spatial location at which at least one subsequent visual stimulus in at least one subsequent measurement cycle is displayed, may be determined by considering at least one particular visual stimulus, particularly by considering an outcome of at least one particular visual stimulus determined in at least one particular measurement cycle. As used herein, the term "outcome" refers to recorded data used in the analysis of the at least one visual performance. The outcome may be recorded continuously during each measurement cycle in such a manner that data recorded during one measurement cycle is continuously added to the outcome. The outcome may thus comprise at least a portion of the data and/or all data recorded in at least a portion of the measurement cycles and/or in all measurement cycles.

In an exemplary embodiment, the second spatial location at which at least one subsequent visual stimulus in at least one subsequent measurement cycle is displayed, may be determined by considering at least one particular visual stimulus by using a psychometric procedure. As generally used, the term "psychometric procedure" refers to a theory-based, standardized test for measuring psychological characteristics of a person. Such a test makes statements about how reliably the characteristic is determined, particularly how reliably the at least one visual performance within the visual field is determined, particularly the at least one visual performance at the at least one point in the visual field. To apply the psychometric procedure, the outcome may be analyzed at least one time during the measurement, particularly the at least one visual parameter may be determined.

In an exemplary embodiment, the psychometric procedure may be selected from at least one of:
- a staircase procedure; or
- a Bayesian method.

As generally used, the term "staircase procedure" refers to a method in which a plurality of stimuli, particularly a modification of the at least on visual stimulus, are presented in ascending and/or descending order in subsequent measurement cycles. When the person's response changes, particularly when the at least one visual stimulus is no longer perceived and/or perceived for the first time, the direction of the stimulus sequence is reversed. As generally used, the term "Bayesian method" refers to a statistical inference procedure in which prior information about at least one population parameter with evidence from information contained in a sample is combined to guide a statistical inference process. Particularly in the context of psychophysical measurements, the term "Bayesian method" refers to a statistical inference procedure in which prior information about a psychometric function parameter space is combined with information from measurement samples, particularly from an outcome generated in a plurality of measurement cycles, to calculate at least one probability distribution of at least one psychometric function parameter and to guide the at least one visual stimulus accordingly, in particular to guide the visual stimulus by varying the at least one parameter and/or the spatial location of the at least one visual stimulus, accordingly.

In an exemplary embodiment, the second spatial location of the at least one visual stimulus may be with regard to the fixation mark in at least one of:
- a top spatial location for determining the at least one visual performance of an inferior visual field;
- a bottom spatial location for determining the at least one visual performance of a superior visual field;
- a left spatial location for determining the at least one visual performance of a nasal visual field or a temporal visual field, respectively; or
- a right spatial location for determining the at least one visual performance of a temporal visual field or a nasal visual field, respectively.

As generally used, the term "inferior visual field" refers to a portion of the visual field above a horizontal line through the line of sight. As generally used, the term "superior visual field" refers to a portion of the visual field below a horizontal line through the line of sight. As generally used, the term "nasal visual field" refers to a portion of the visual field lateral to a vertical line through the line of sight on the side where the nose is. As generally used, the term "temporal visual field" refers to a portion of the visual field lateral to a vertical line through the line of sight on the side where the temple is. In an exemplary embodiment, from at least one outcome generated in four measurement cycles as well the top spatial location, the bottom spatial location, the left spatial location and the right spatial location of the at least one visual performance may be determined.

In an exemplary embodiment, the fixation mark may be a particular item designated for directing the view, particularly the gaze position, of the at least one eye thereto, typically wherein the at least one fixation mark may be selected from at least one of:
- at least one of an artificial pattern;
- a specific natural image; or
- a specific virtual image;

specifically,
- a fixation cross;
- a circle, particularly a blank circle;
- a dot; or
- a cartoon.

In an exemplary embodiment, in at least two measurement cycles and/or in all measurement cycles comprising step a) the at least one fixation mark may be displayed at the same first spatial location. In an exemplary embodiment, a reaction time may be determined, particularly during step b) for determining the visual attention, wherein the reaction time is a time difference between displaying the at least one visual stimulus on the at least one screen and an occurrence of the at least one eye movement, in particular the occurrence of the at least one eye movement as elicited by the at least one visual stimulus. In an exemplary embodiment, the reaction time may be a time difference between a beginning of the displaying of the at least one visual stimulus on the at least one screen and the beginning of the at least one eye movement, in particular the beginning of the at least one eye movement that has been elicited by the at least one visual stimulus.

In an exemplary embodiment, a flag may categorize the at least one visual stimulus displayed during step b) as "seen", when the at least one eye movement has been tracked during displaying the at least one visual stimulus, in particular when the at least one eye movement has been elicited by the at least one visual stimulus. As generally used, the term "flag" refers to a status indicator that is may be used as a tool to indicate a certain states, particularly a status of the occurrence of the at least one eye movement. A flag may be set, deleted or checked. In an exemplary embodiment, a flag may categorize the at least one visual stimulus displayed during step b) as "not seen", when the at least one eye movement has not been tracked during displaying the at least one visual stimulus, in particular when the at least one eye movement has not been elicited by the at least one visual stimulus.

In an exemplary embodiment, step b) may comprise emitting an attention stimulus configured direct a focus of the person to an upcoming displaying of the at least one visual stimulus. As used herein, the term "emitting" refers to the issuing the attention stimulus perceivable by the person. As generally used, the term "focus" refers to the center of interest or activity of the person. It may refer to the ability of the person to concentrate on the next visual stimulus, wherein the next visual stimulus is not yet displayed at the point in time at which the attention stimulus is emitted but will be displayed after emitting the at least one visual stimulus.

In an exemplary embodiment, the attention stimulus may be selected from at least one of:
  a visual signal;
  an audio signal; or
  a tactile signal.

As used herein, the term "visual signal" refers to an attention stimulus that is displayed to the at least one eye of the person. The term "audio signal" is an attention stimulus that is perceptible by a sense of hearing of the person. The term "tactile signal" refers to an attention stimulus that is perceived by a haptic sensation, for example haptic sensations such as, but not limited to, tickling, a touch, a movement, a vibration, a temperature, a pressure and/or a tension.

In an exemplary embodiment, determining the at least one visual performance may comprise analyzing the at least one outcome. In an exemplary embodiment, at least one outcome may be generated which comprises for at least one circle at least one of:
  the visual stimulus;
  the tracking data, particularly selected from:
  a time variance of the gaze position; or
  a time variance of the line of sight;
  the second spatial location of the at least one visual stimulus, in particular a center of the at least one visual stimulus;
  the flag;
  the first threshold;
  the second threshold.

the pupil size;
  the reaction time; or
  the attention stimulus.

As used herein, the term "generating" or any grammatical deviation thereof refers to recording the measured data. The at least one outcome may comprise data recorded in a plurality of measurement cycles. As generally used, the term "analyzing" or any grammatical variation thereof refers to a systematic investigation in which the at least one outcome under investigation is broken down into its components. These components are thereby recorded on the basis of criteria and subsequently ordered, examined and evaluated.

In an exemplary embodiment, at least one outcome may be generated that comprises for the at least one circle:
  the tracking data; particularly selected from:
  a time variance of the gaze position; or
  a time variance of the line of sight; and
  the second spatial location of the at least one visual stimulus, in particular of a center of the at least one visual stimulus.

In an exemplary embodiment, a plurality of reaction times of the at least one particular measurement cycle and/or wherein a plurality of reaction times of the at least one subsequent measurement cycle may be correlated, in particular correlated by
  calculating a mean-value;
  determining a maximal value; or
  determining a minimal value.

As used herein, the term "correlate" refers to a mutual interaction of information, which is implemented in such a manner that the interaction generates an output. The term "mean-value" refers to a scaled sum, particularly the sum of the values scaled by dividing by the number of values. The term "maximal value" refers to the largest value. The term "minimal value" refers to the smallest value.

In an exemplary embodiment, the at least one subsequent measurement cycle may be performed later than the at least one particular measurement cycle by a time interval of at least 1 min, 2 min, 3 min, 4 min, 5 min, 6 min, 7 min, 8 min, 9 min, 10 min, 15 min, 20 min or 30 min. As generally used, the term "time interval" refers to a definite length of time marked off by two time stamps.

According to a further aspect, the present disclosure relates to a computer program comprising instructions which, when the program is executed by a computer, cause the computer to carry out at least one step, typically all steps, of the computer-implemented method for determining at least one visual performance of at least one eye of a person as disclosed herein. For this purpose, a computer program may comprise instructions provided by means of a computer program code which are capable of performing any or all of the steps of the methods according to the present disclosure when implemented on a computer or a data processing device. The computer program code may be provided on a data storage medium or a separate device such as an optical storage medium, e.g. on a compact disc, directly on a computer or data processing device, or via a network, such as via an in-house network or via internet. For further details concerning the computer program, reference may be made to the methods according to the present disclosure as disclosed elsewhere herein.

According to a further aspect, the present disclosure relates to an apparatus for determining at least one visual performance of at least one eye of a person, the apparatus comprising:
  at least one screen configured for displaying to the at least one eye of a person at least one visual fixation mark configured to attract a visual perception of the person by directing a line of sight of the at least one eye of the person towards the visual fixation mark; and subsequently at least one visual stimulus configured to elicit at least one eye movement in the at least one eye of the person;

at least one eye-tracking device configured for generating tracking data about the at least one eye movement of the at least one eye of the person moving towards the at least one visual stimulus;

at least one processing device configured for determining the at least one visual performance from the tracking data;

wherein the at least one processing device is configured for determining the at least one visual performance of the at least one eye of the person for at least one point in a visual field of the person by using a first spatial location of the at least one visual fixation mark and a second spatial location of the at least one visual stimulus; wherein an attention level of the person is determined by evaluating a time-related difference in the reaction times between the at least one particular measurement cycle and the at least one subsequent measurement cycle.

In an exemplary embodiment, the apparatus further may comprise at least one of:

at least one connecting interface configured for transferring at least one outcome generated for at least one measurement cycle to a remote apparatus configured to determine the visual performance of the at least one eye of the person;

at least one distance measuring device configured for measuring a distance between the at least one eye of the person and the at least one visual stimulus and/or the at least one visual fixation mark.

As generally used, the term "connecting interface" refers to shared boundary across which two or more separate components of a computer system exchange information. The exchange can be between software, computer hardware, peripheral devices, humans, and combinations of these.

In an exemplary embodiment, the connecting interface may be selected from at least one of:

a network interface controller; or a transmitter.

As generally used, the term "network interface controller" refers to a computer hardware component that connects a computer to a computer network. As generally used, the term "transmitter" refers to an electronic device, which produces electromagnetic waves with an antenna.

In an exemplary embodiment, the apparatus may be selected from at least one of:

a system comprising a stand-alone computer, a monitor, and a camera;

a system comprising a personal computer, a monitor, and a camera;

a virtual reality headset;

an augmented reality overlay device;

a television set; or or a mobile communication device.

As used herein, the term "stand-alone computer" refers to a computer that is not necessarily connected to any other computer. Users can interact with the stand-alone computer, enter and process data, but no data or information is exchanged with other computers in the process of determining the visual performance within a visual field of at least one eye of a person. As generally used, the term "personal computer" refers to a multifunctional computer with a geometry and capabilities making it useful in everyday situations. As generally used, the term "virtual reality headset" refers to a head-mounted device that provides virtual reality for the wearer. As generally used, the term "augmented reality overlay device" refers to a hardware for an interactive experience between a real-world environment and computer-generated perceptual information. As generally used, the term "television set" refers to a device having a tuner, a display and at least one loudspeaker for a purpose of viewing and listening to television broadcasting through at least one of satellite or cable, wherein the television set may also be used as a monitor. As generally used, the term "mobile communication device" refers to a portable wireless telecommunications equipment that may transmit and/or receive voice, video, or computer data.

In an exemplary embodiment, the mobile communication device may be selected from at least one of:

a smartphone;

a tablet; or a laptop.

As generally used, the term "smartphone" refers to a mobile phone having extensive computer functionalities and connectivity. As generally used, the term "tablet" refers to a portable, flat touch-screen computer. As generally used, the term "laptop" refers to a special type of computer having a screen movably attached to a housing, wherein the screen may be folded onto the housing.

In an exemplary embodiment, the at least one screen may be selected from at least one of:

a monitor;

a virtual reality head set;

a touchscreen; or a projector.

As generally used, the term "monitor" refers to an electrically controlled display for a visual displaying of information such as an image or an item. As generally used, the term "touchscreen" refers to device having a screen that can be touch to generate an input. As generally used, the term "projector" refers to an optical device for enlarging a two-dimensional original by suitable guidance of light rays.

In an exemplary embodiment, the at least one eye-tracking device may be selected from at least one of:

a camera;

a webcam;

eye tracking glasses; or a visually evoked potential device.

As generally used, the term "camera" refers to an optical device that captures visual images. As generally used, the term "webcam" refers to a small camera that may sit on a monitor, or is built into a computer. As generally used, the term "eye tracking glasses" refers to a spectacle having an attached sensor for tracking an eye. As generally used, the term "visually evoked potential device" refers to a device configured for recording of a specific part of the nervous system.

In an exemplary embodiment, the apparatus may be configured for carrying out at least one step, typically all steps, of the computer-implemented method for determining at least one visual performance within a visual field of at least one eye of a person.

According to a further aspect, the present disclosure relates to a remote apparatus for determining at least one visual performance of at least one eye of a person, the remote apparatus is comprising:

at least one connecting interface for receiving at least one recorded outcome generated by at least one apparatus for determining at least one visual performance of at least one eye of a person as described elsewhere herein; and at least one processing device configured to determine the at least one visual performance within the visual field of at least one eye of a person by using the at least one recorded outcome.

As generally used, the term "receiving" refers taking and beginning to process the at least one outcome provided by computer-implemented method for determining the at least one visual performance within the visual field of the at least one eye of a person.

In an exemplary embodiment, the connecting interface may be selected from at least one of:
a network interface controller; or
a transmitter.

With respect to the prior art, the device exhibits the following advantages.

Visual performance tests for determining a visual performance for a specific point in a visual field as known from the state of art mostly require an ophthalmologist or optometry specialist. Therefore, such test result in reduced portability and cannot be performed by a person itself. The automated test of the present disclosure on the other hand may be performed by the person itself, particularly by using a mobile device.

As the eye movement is measured directly using an eye tracking device, the test has the advantage that it does not require any further response of the patient. This makes testing of children or patients with disabilities easier.

The visual performance may be determined for the peripheral field of view as the determination is carried out in a spatially resolved manner in such a way that the visual performance is assigned to a point in the visual field.

The testing is time efficient, as a one-trial-only testing procedure may be performed, particularly in combination with a smooth enhancement of the visual stimulus, and particularly by considering the first threshold and the second threshold as well as psychometric procedures. It is further possible to monitor a time dependency of the visual field.

As used herein, the terms "have", "comprise" or "include" or any arbitrary grammatical variation thereof are used in a non-exclusive way. Thus, these terms may refer to both a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

As further used herein, the terms "preferably", "more preferably", "particularly", "more particularly", or similar terms are used in conjunction with optional features, without restricting alternative possibilities. Thus, features introduced by these terms are optional features and are not intended to restrict the scope of the claims in any way. The disclosure may, as the skilled person will recognize, be performed by using alternative features. Similarly, features introduced by "in an embodiment of the disclosure" or similar expressions are intended to be optional features, without any restriction regarding alternative embodiments of the disclosure, without any restrictions regarding the scope of the disclosure and without any restriction regarding the possibility of combining the features introduced in this way with other features of the disclosure.

Summarizing, the exemplary embodiments according to the following clauses are particularly typical within the scope of the present disclosure:

Clause 1. A computer-implemented method for determining at least one visual performance of at least one eye of a person, wherein the method comprises at least the following steps:
a) displaying on a screen to the at least one eye of a person at least one visual fixation mark configured to attract a visual perception of the person by directing a line of sight of the at least one eye of the person towards the visual fixation mark; subsequently displaying on the screen to the at least one eye of the person at least one visual stimulus configured to elicit at least one eye movement in the at least one eye of the person towards the at least one visual stimulus;
b) generating tracking data about the at least one eye movement of the at least one eye of the person by using at least one eye-tracking device; and
c) determining the at least one visual performance from the tracking data by using at least one processing device;
d) wherein the at least one visual performance of the at least one eye of the person is determined for at least one point in a visual field of the person by using a first spatial location of the at least one visual fixation mark and a second spatial location of the at least one visual stimulus.

Clause 2. The method according to the preceding Clause, wherein the first spatial location of the at least one visual fixation mark is recorded during step a) and the second spatial location of the at least one visual stimulus is recorded during step b).

Clause 3. The method according to any one of the preceding Clauses, wherein the at least one visual performance is determined for a particular point in the visual field by assigning a particular point using an assignment rule.

Clause 4. The method according to any one of the preceding Clauses, wherein the assignment rule considers the second spatial location of the at least one visual stimulus and first the spatial location of the at least one visual fixation mark; and particularly further considers a distance between the at least one eye of the person and the at least one visual stimulus and/or the at least one visual fixation mark.

Clause 5. The method according to any one of the preceding Clauses, wherein a measurement cycle comprises at least step b) and step c), wherein the measurement cycle may further comprises at least one of step a) or step d), wherein at least two measurement cycles are performed for determining a plurality of points in the visual field, typically with a differing second spatial location of the at least one visual stimulus.

Clause 6. The method according to any one of the preceding Clauses, wherein the assignment rule is maintained during the at least two measurement cycles and/or in all measurement cycles.

Clause 7. The method according to any one of the preceding Clauses, wherein at least one of: 2; 3; 4; 5; 7; 10; 15; 20; 25; 50; 75; or 100 measurement cycles are performed.

Clause 8. The method according to any one of the preceding Clauses, wherein the at least one visual fixation mark is displayed in a center area of the screen, particularly directing the at least one eye of the person in a neutral position.

Clause 9. The method according to any one of the preceding Clauses, wherein the center area is completely enclosed by a surrounding area, wherein the at least one visual stimulus is displayed in the surrounding area in step b).

Clause 10. The method according to any one of the preceding Clauses, wherein an angle α is given between a first connecting line and a second connecting line, wherein the first connecting line connects a center of the at least one visual fixation mark and at least one reference position in the at least one eye of the person, wherein the second connecting line connects a center of the at least one visual stimulus and the at least one reference position in the at least one eye of the person, wherein a is larger than at least one of: 2°; 3°; 4°; 5°; 6°; 7°; or 8°.

Clause 11. The method according to any one of the preceding Clauses, wherein the at least one reference position in the at least one eye of the person is selected from at least one of:
a pupil center;
a corneal reflex; or
a corneal apex.

Clause 12. The method according to any one of the preceding Clauses, wherein the at least one visual stimulus can be display in any spatial orientation with regard to the at least one visual fixation mark.

Clause 13. The method according to any one of the preceding Clauses, wherein the surrounding area corresponds to the peripheral field of view, when the line of sight of the at least one eye of the person intersects with the at least one visual fixation mark.

Clause 14. The method according to any one of the preceding Clauses, wherein a third connecting line connecting an outer perimeter of the central field of view, particularly connecting a maximal circumference of the central field of view, and a reference position in the at least one eye of the person is given, wherein a central field of view angle between the third connecting line and the line of sight of the at least one eye of the person that intersects the reference position in the at least one eye of the person, is at least one of: 2°; 3°; 4°; 5°; 6°; 7° or 8°.

Clause 15. The method according to any one of the preceding Clauses, wherein the visual performance of the at least one eye of the person is selected from at least one of:
a contrast sensitivity;
a visual acuity;
a color vision;
a time-related sensitivity; or
a visual attention.

Clause 16. The method according to any one of the preceding Clauses, wherein the at least one eye movement is a reflexive saccade in the at least one eye of the person.

Clause 17. The method according to any one of the preceding Clauses, wherein a pupil size of the at least one eye of the person is further recorded, particularly a time-variance of the pupil size of the at least one eye of the person.

Clause 18. The method according to the any one of the preceding Clauses, wherein the at least one visual stimulus is continuously displayed during step b).

Clause 19. The method according to the any one of the preceding Clauses, wherein the at least one visual stimulus is selected from at least one of:
at least one of an artificial pattern;
a specific natural image; or
a specific virtual image;
specifically,
a grating, particularly a Gabor patch;
a noise patch having at least one defined spatial frequency.

Clause 20. The method according to any one of the preceding Clauses, wherein an appearance of the at least one visual stimulus is displayed in a time-varying manner on the at least one screen.

Clause 21. The method according to any one of the preceding Clauses, an appearance of the at least one visual fixation mark on the at least one screen and the appearance of the at least one visual stimulus on the at least one screen are different from each other.

Clause 22. The method according to any one of the preceding Clauses, wherein the at least one visual fixation mark is maintained in a constant manner during at least one measurement cycle.

Clause 23. The method according to any one of the preceding Clauses, wherein at least one parameter attributed to the appearance of the at least one visual stimulus is varied between a first value and a second value, particularly in a continuous manner, more particularly in a monotonous manner.

Clause 24. The method according to any one of the preceding Clauses, wherein the at least one parameter is selected from at least one of:
a contrast, in particular for determining the contrast sensitivity;
a spatial frequency, in particular for determining the visual acuity;
a color, in particular for determining the color vision; or
a time-related frequency, in particular for determining a time-related sensitivity.

Clause 25. The method according to any one of the preceding Clauses, wherein for the at least one parameter attributed to the appearance at least one of:
a first threshold is determined at which the at least one eye movement in the at least one eye of the person is tracked for the first time; or
a second threshold value is determined at which the at least one eye movement in the at least one eye of the person is tracked for the last time.

Clause 26. The method according to any one of the preceding Clauses, wherein a plurality of at least one parameter is attributed to the appearance, particularly wherein a plurality of at least one parameter attributed to the appearance is varied between a first value and a second value, particularly in a continuous manner, more particularly in a monotonous manner.

Clause 27. The method according to any one of the preceding Clauses, wherein step c) is performed during at least one of:
step a); or
step b).

Clause 28. The method according to any one of the preceding Clauses, wherein displaying of the at least one visual fixation mark is stopped before step b).

Clause 29. The method according to any one of the preceding Clauses, wherein a gaze position of the at least one eye of the person is checked during step a).

Clause 30. The method according to any one of the preceding Clauses, wherein the center of the fixation mark is displayed in a central field of view during step a).

Clause 31. The method according to any one of the preceding Clauses, wherein the gaze position is checked whether it is inside or outside an area of the at least one visual fixation mark during step a); particularly step b) is only performed when the gaze position is inside the area of the at least one visual fixation mark.

Clause 32. The method according to any one of the preceding Clauses, wherein the area of the at least one visual fixation mark is at least partially and/or completely located within the central field of view.

Clause 33. The method according to any one of the preceding Clauses, wherein the visual performance of the at least one eye is determined outside the central field of view in the peripheral field of view.

Clause 34. The method according to any one of the preceding Clauses, wherein the center and/or the area of the at least one visual stimulus is displayed in the peripheral field of view during step b).

Clause 35. The method according to any one of the preceding Clauses, wherein displaying the at least one visual stimulus during step b) is stopped when the at least one eye movement has been tracked, in particular when the at least one eye movement has been elicited by the at least one visual stimulus.

Clause 36. The method according to any one of the preceding Clauses, wherein during step b) the at least one visual stimulus is displayed for a maximum of a predetermined time.

Clause 37. The method according to any one of the preceding Clauses, wherein step b) is repeated when at least one visual disturbance which affects the ability of the at least one eye of a person to observe the visual stimulus is detected.

Clause 38. The method according to any one of the preceding Clauses, wherein the at least one visual disturbance is selected from at least one of:
  a blink of the at least one eye of the person;
  a gaze position of the at least one eye of the person outside of the screen displaying the visual stimulus;
  a vergence angle between both eyes of the person showing that the person is not focusing on the screen; or
  a pupil size showing that the person is not focusing on the screen.

Clause 39. The method according to any one of the preceding Clauses, wherein during step b) the second spatial location of the at least one visual stimulus is maintained.

Clause 40. The method according to any one of the preceding Clauses, wherein the second spatial location at which the at least one visual stimulus is displayed is determined randomly by an algorithm.

Clause 41. The method according to any one of the preceding Clauses, wherein the second spatial location at which at least one subsequent visual stimulus in at least one subsequent measurement cycle is displayed is determined by considering at least one particular visual stimulus, particularly by considering an outcome of at least one particular visual stimulus determined in at least one particular measurement cycle.

Clause 42. The method according to any one of the preceding Clauses, wherein the second spatial location at which at least one subsequent visual stimulus in at least one subsequent measurement cycle is displayed is determined by considering at least one particular visual stimulus by using a psychometric procedure.

Clause 43. The method according to any one of the preceding Clauses, wherein the psychometric procedure is selected from at least one of:
  a staircase procedure; or
  a Bayesian method.

Clause 44. The method according to any one of the preceding Clauses, wherein the second spatial location of the at least one visual stimulus is with regard to the fixation mark in at least one of:
  a top spatial location for determining the at least one visual performance of an inferior visual field;
  a bottom spatial location for determining the at least one visual performance of a superior visual field;
  a left spatial location for determining the at least one visual performance of a nasal visual field or a temporal visual field, respectively; or
  a right spatial location for determining the at least one visual performance of a temporal visual field or a nasal visual field, respectively.

Clause 45. The method according to any one of the preceding Clauses, wherein from at least one outcome generated in four measurement cycles as well the top spatial location, the bottom spatial location, the left spatial location and the right spatial location the visual performance is determined.

Clause 46. The method according to any one of the preceding Clauses, wherein the fixation mark is a particular item designated for directing the view, particularly the gaze position, of the at least one eye thereto, typically wherein the at least one fixation mark is selected from at least one of:
  at least one of an artificial pattern;
  a specific natural image; or
  a specific virtual image;
specifically,
  a fixation cross;
  a circle, particularly a blank circle;
  a dot; or
  a cartoon.

Clause 47. The method according to any one of the preceding Clauses, wherein in the at least two measurement cycles and/or in all measurement cycles further comprising step a) the at least one fixation mark is displayed at the same first spatial location.

Clause 48. The method according to any one of the preceding Clauses, wherein a reaction time is determined during step b) for determining the visual attention, wherein the reaction time is a time difference between displaying the at least one visual stimulus on the at least one screen and an occurrence of the at least one eye movement, in particular the occurrence of the at least one eye movement as elicited by the at least one visual stimulus.

Clause 49. The method according to any one of the preceding Clauses, wherein the reaction time is a time difference between a beginning of the displaying of the at least one visual stimulus on the at least one screen and the beginning of the at least one eye movement, in particular the beginning of the at least one eye movement that has been elicited by the at least one visual stimulus.

Clause 50. The method according to any one of the preceding Clauses, wherein a flag categorizes the at least one visual stimulus displayed during step b) as "seen", when the at least one eye movement has been tracked during displaying the at least one visual stimulus, in particular when the at least one eye movement has been elicited by the at least one visual stimulus.

Clause 51. The method according to any one of the preceding Clauses, wherein a flag categorizes the at least one visual stimulus displayed during step b) as "not seen", when the at least one eye movement has not been tracked during displaying the at least one visual stimulus, in particular when the at least one eye movement has not been elicited by the at least one visual stimulus.

Clause 52. The method according to any one of the preceding Clauses, wherein step b) comprises emitting an attention stimulus configured to direct a focus of the person to an upcoming displaying of the at least one visual stimulus.

Clause 53. The method according to any one of the preceding Clauses, wherein the attention stimulus is selected from at least one of:
 a visual signal;
 an audio signal; or
 a tactile signal.

Clause 54. The method according to any one of the preceding Clauses, wherein determining the at least one visual performance comprises analyzing the at least one outcome.

Clause 55. The method according to any one of the preceding Clauses, wherein the at least one outcome is generated that comprises for at least one circle at least one of:
 the visual stimulus;
 the tracking data generated by the eye tracking device, particularly selected from:
 a time variance of the gaze position; or
 a time variance of the line of sight;
 the second spatial location of the at least one visual stimulus, in particular of the center of the at least one visual stimulus;
 the flag;
 the first threshold;
 the second threshold.
 the pupil size;
 the reaction time; or
 the attention stimulus.

Clause 56. The method according to any one of the preceding Clauses, wherein at least one outcome is generated that comprises for the at least one circle:
 the tracking data generated by the eye tracking device, particularly selected from:
 a time variance of the gaze position; or
 a time variance of the line of sight; and
 the second spatial location of the at least one visual stimulus, in particular of the center of the at least one visual stimulus.

Clause 57. The method according to any one of the preceding Clauses, wherein an attention level of the person is determined by evaluating a time-related difference in the reaction times between the at least one particular measurement cycle and the at least one subsequent measurement cycle.

Clause 58. The method according to any one of the preceding Clauses, wherein a plurality of reaction times of the at least one particular measurement cycle and/or wherein a plurality of reaction times of the at least one subsequent measurement cycle are correlated, particularly correlated by
 calculating a mean-value;
 determining a maximal value; or
 determining a minimal value.

Clause 59. The method according to any one of the preceding Clauses, wherein the at least one subsequent measurement cycle is performed later than the at least one particular measurement cycle by a time interval of at least 1 min, 2 min, 3 min, 4 min, 5 min, 6 min, 7 min, 8 min, 9 min, 10 min, 15 min, 20 min, or 30 min.

Clause 60. A computer program comprising instructions which, when the program is executed by a computer, cause the computer to carry out a method according to any one of the preceding method Clauses.

Clause 61. An apparatus for determining at least one visual performance of at least one eye of a person, the apparatus comprising:
 at least one screen configured for displaying to the at least one eye of a person;
 at least one visual fixation mark configured to attract a visual perception of the person by directing a line of sight of the at least one eye of the person towards the visual fixation mark; and
 subsequently at least one visual stimulus configured to elicit at least one eye movement in the at least one eye of the person;
 at least one eye-tracking device configured for generating tracking data about the at least one eye movement of the at least one eye of the person moving towards the at least one visual stimulus;
 at least one processing device configured for determining the at least one visual performance from the tracking data;
wherein the at least one processing device is configured for determining the at least one visual performance of the at least one eye of the person for at least one point in a visual field of the person by using a first spatial location of the at least one visual fixation mark and a second spatial location of the at least one visual stimulus.

Clause 62. The apparatus according to the preceding Clause, wherein the apparatus further comprises at least one of:
 at least one connecting interface configured for transferring at least one outcome generated for at least one measurement cycle to a remote apparatus configured to determine the visual performance of the at least one eye of the person; or
 at least one distance measuring unit configured for measuring a distance between the at least one eye of the person and the at least one visual stimulus and/or the at least one visual fixation mark.

Clause 63. The apparatus according to the preceding Clause, wherein the connecting interface is selected from at least one of:
 a network interface controller; or
 a transmitter.

Clause 64. The apparatus according to any one of the preceding apparatus Clauses, wherein the apparatus is selected from at least one of:
 a system comprising a stand-alone computer, a monitor, and a camera;
 a system comprising a personal computer, a monitor, and a camera;
 a virtual reality headset;
 an augmented reality overlay device;
 television set; or
 or a mobile communication device.

Clause 65. The apparatus to any one of the preceding apparatus Clauses, wherein the mobile communication device is selected from at least one of:
 a smartphone;
 a tablet; or
 a laptop.

Clause 66. The apparatus to any one of the apparatus preceding Clauses, wherein the at least one screen is selected from at least one of:
- a monitor;
- a virtual reality head set;
- a touchscreen; or
- a projector.

Clause 67. The apparatus to any one of the preceding apparatus Clauses, wherein the at least one eye-tracking device is selected from at least one of:
- a camera;
- a webcam;
- eye tracking glasses; or
- a visually evoked potential device.

Clause 68. The apparatus according to any one of the apparatus device Clauses, wherein the apparatus is configured for carrying out a method according to any one of the preceding method Clauses.

Clause 69. A remote apparatus for determining at least one visual performance of at least one eye of a person, the remote apparatus comprising:
- at least one connecting interface for receiving at least one recorded outcome generated by at the apparatus of any one of the preceding apparatus Clauses; and
- at least one processing device determining the at least one visual performance by using the at least one recorded outcome.

Clause 70. The remote apparatus according to the preceding Clause, wherein the connecting interface is selected from at least one of:
- a network interface controller; or
- a transmitter.

BRIEF DESCRIPTION OF THE DRAWINGS

Further optional features and configurations of the present disclosure are disclosed in more detail in the subsequent description of exemplary embodiments. Therein, the respective optional features may be realized in an isolated fashion as well as in any arbitrary feasible combination, as the skilled person will realize. It is emphasized here that the scope of the disclosure is not restricted by the exemplary embodiments. In the drawings.

DESCRIPTION OF EXEMPLARY EMBODIMENTS

Figure 1:
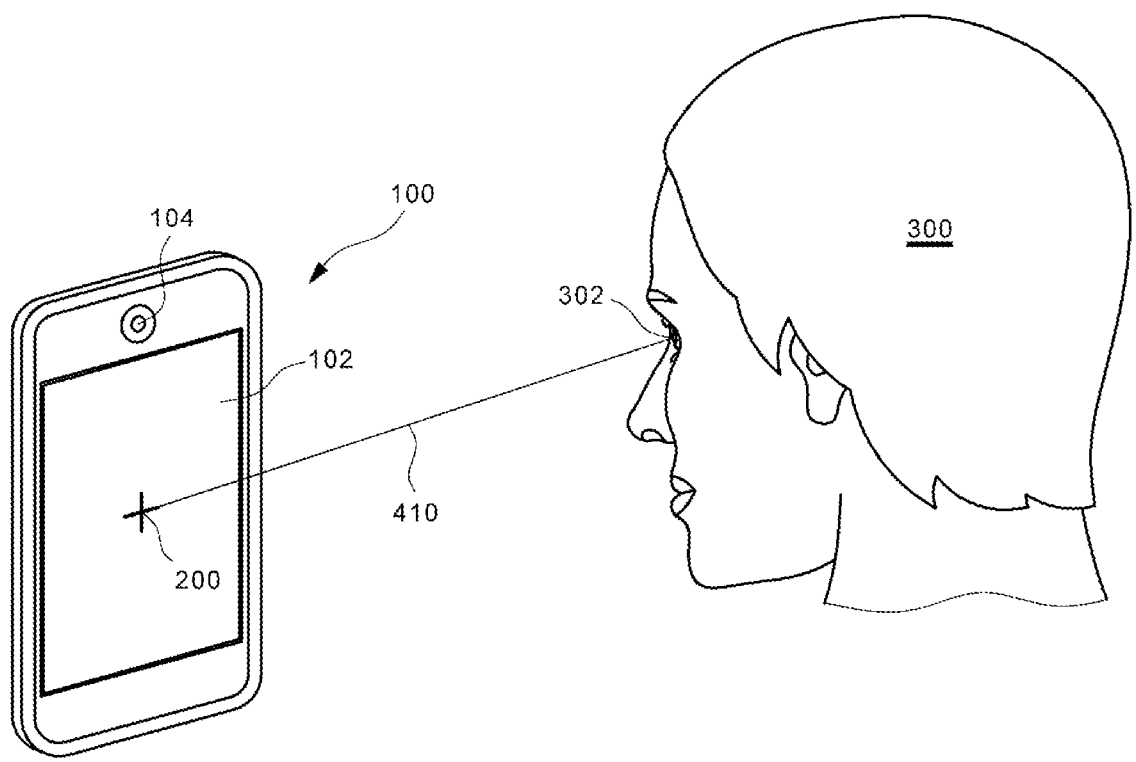
FIG. 1 illustrates an aerial view of an exemplary apparatus for determining at least one visual performance of at least one eye of a person.

FIG. 1 shows an exemplary apparatus 100 for determining a visual performance within a visual field 400, 402 of an eye 302 of a person 300. The apparatus 100 according to FIG. 1 is a mobile communication device, especially a smartphone. Alternatively, the apparatus 100 may be a system comprising a stand-alone computer, a monitor, and a camera; a system comprising a personal computer, a monitor, and a camera; a virtual reality headset; an augmented reality overlay device; a television set; a tablet; or a laptop.

The visual performance which is exemplarily determined here is a visual acuity in the peripheral field of view 402. Alternatively or in addition, a contrast sensitivity, a color vision, a time-related sensitivity and/or a visual attention may be determined.

The apparatus 100 comprises a screen 102 according to FIG. 1. On the screen 102 a visual fixation mark 200 is displayed to the eye 302 of the person 300. To determine the visual performance, a visual stimulus 210 is, subsequently, displayed on the screen 102 in order to elicit an eye movement in the eye 302 of the person 300 (not depicted here). The screen 102 as depicted in FIG. 1 is a touchscreen of the smartphone. Alternatively, the screen 102 may be a monitor, a virtual reality head set, a television set, or a projector.

The apparatus 100 comprises an eye-tracking device 104 configured for tracking the eye movement in the eye 302 of the person 300. The eye-tracking device 104 according to FIG. 1 is a camera integrated into the smartphone. Alternatively, the eye-tracking device 104 may be a webcam, an eye tracking glasses, or a visually evoked potential device. The eye-tracking device 104 according to FIG. 1 is further used as a distance measuring unit. For this purpose, it is configured for measuring and recording a distance between the eye 302 of the person 300 and the visual stimulus 210. Further, the distance between the visual fixation mark 200 the eye 302 of the person 300 can be measured and recorded.

To determine the visual performance within the visual field 400, 402 of the eye 302 of the person 300, a computer-implemented method 500 may be applied. The method 500 may be implemented as a computer program that is running on the apparatus 100.

Figure 2A:
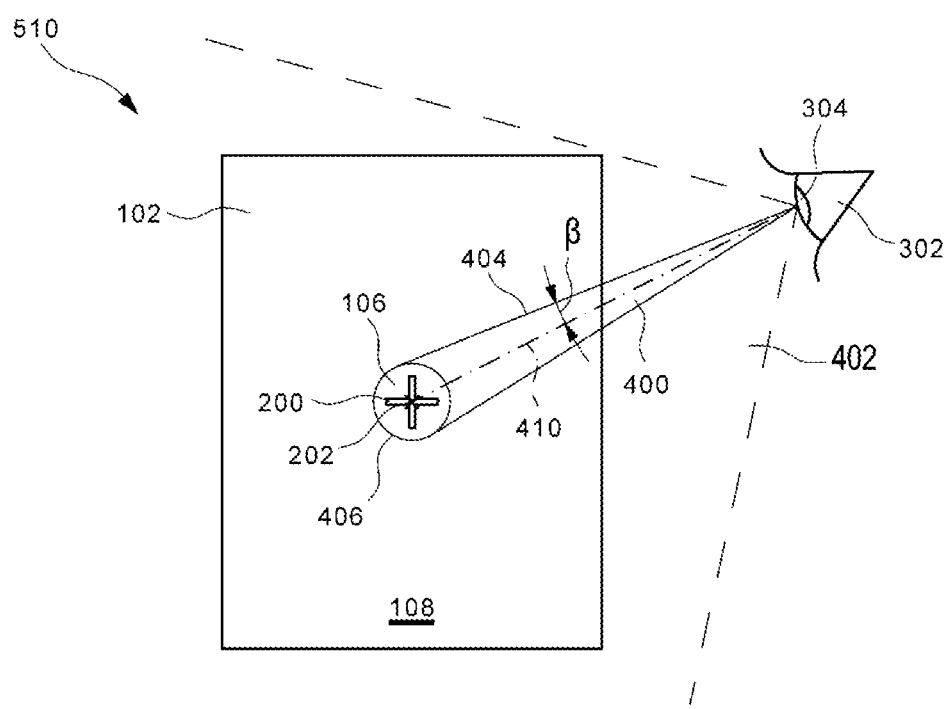
FIGS. 2A to 2C illustrate a schematic view of a generating step (FIG. 2A) and a second displaying step (FIGS. 2B and 2C) of a method for determining at least one visual performance of at least one eye of a person implemented as a computer program running on the apparatus.

According to FIG. 2A, in a first displaying step 510 according to step a) of the method 500 the visual fixation mark 200 is displayed on the screen 102 to the eye 302 of the person 300. The fixation mark 200 as depicted here is an artificial pattern, specifically a fixation cross. Alternatively, the fixation mark 200 may be a specific natural image, a specific virtual image, a circle, particularly a blank circle, a dot, or a cartoon. The fixation mark 200 is displayed in a center area 106 of the screen 102. The spatial location of the visual fixation mark 200 is maintained in a constant manner during at least one measurement cycle 550, typically a plurality of measurement cycles 550. A first spatial location of the visual fixation mark 200 is recorded.

The fixation mark 200 is designated for directing the view, particularly a gaze position, of the eye 302 thereto. In FIG. 2A, the gaze position is in an area defined by the visual fixation mark 200 and therefore a line of sight 410 of the eye 302 intersects with the visual fixation mark 200. The eye 302 is in a neutral position. As a result, the center 202 of the visual fixation mark 200 is displayed in a central field of view 400 of the eye 302 of the person 300 during the first displaying step 510. The area of the visual fixation mark 200 is completely located within the central field of view 400. The center area 106 of the screen 102 corresponds to the central field of view 400.

The central field of view 400 is defined by a central field of view angle ß between a third connecting line 404, connecting an outer perimeter 406 of the central field of view 400 and the line of sight 410 of the eye 302 of the person 300 that goes through the reference position in eye 302 of the person 300. The outer perimeter 406 may be a maximal circumference of the central field of view 400. The central field of view angle β as depicted in FIG. 2A is 4°.

Alternatively, the central field of view angle β may be 2°, 3°; 5°; 6°; 7° or 8°. The reference position in the eye 302 may be a pupil center, a corneal reflex, or a corneal apex.

The eye-tracking device 104 is further used to check if a gaze position of the eye 302 is whether inside or outside an area comprising a second spatial location of a center 202 of the visual fixation mark 200 during the first displaying step 510. When the gaze position is inside the area of the visual fixation mark 200 a second displaying step 520 according to step b) of the method 500 may be performed.

Figure 2B:
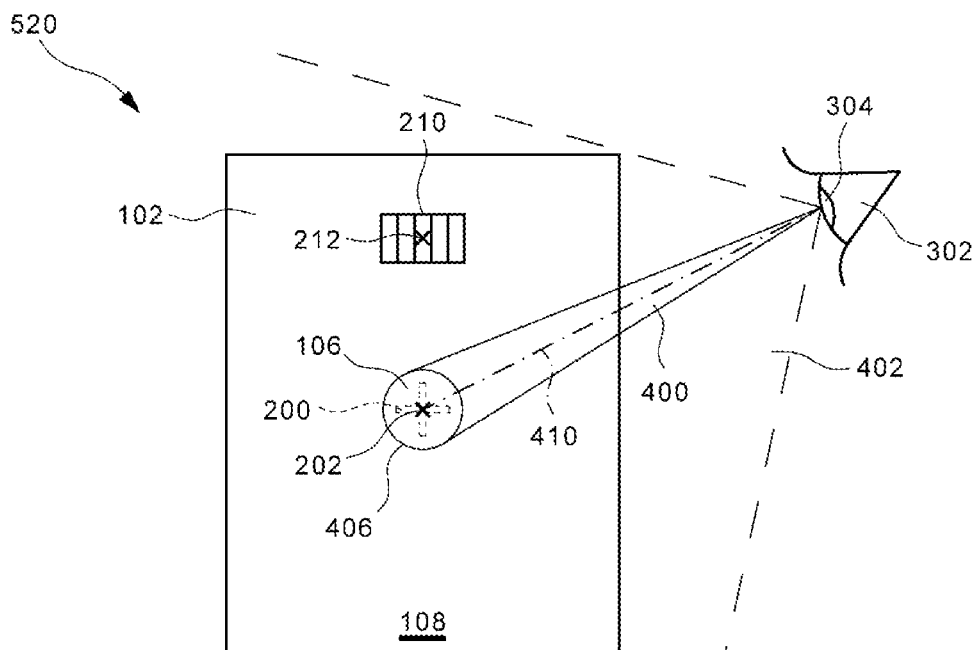

According to a second displaying step 520 of the method 500, the visual stimulus 210 is displayed on the screen 102 to elicit an eye movement in the eye 302 of the person 300 as depicted in FIG. 2B. The expected eye movement is a reflexive saccade. As can be seen in the FIGS. 2B and 2C, displaying of the visual fixation mark 200 is stopped before the second displaying step 520 and therefore the visual fixation mark 200 is indicated in these drawings by dashed lines. Alternatively, the visual fixation mark 200 may be displayed during the second displaying step 520.

The visual stimulus 210 depicted in FIG. 2B is an artificial pattern, specifically a grating being a Gabor patch. Alternatively, the visual stimulus 210 may be a specific natural image, a specific virtual image, or a noise patch having at least one defined spatial frequency. The appearance of the visual fixation mark 200 and the appearance of the at least one visual stimulus 210 is different from each other.

The visual stimulus 210 may be displayed outside of the central field of view 400 in the peripheral field of view 402. The second spatial location of the visual stimulus 210 may be located in a surrounding area 108 that completely encloses the center area 106. This can be achieved by considering an angle α, which is defined between a first connecting line 220 and a second connecting line 230. The first connecting line 220 connects the center 202 of the visual fixation mark 200 and a reference position in the eye 302 of the person 300. The second connecting line 230 connects the center 212 of the visual stimulus 210 and the reference position in the eye 302 of the person 300. As the visual stimulus 210 is displayed in the peripheral field of view 402, the angle α is, according to FIG. 2B, larger than 4°. Alternatively, it may be larger than 2°, 3°, 5°, 6°, 7° or 8°.

Figure 2C:
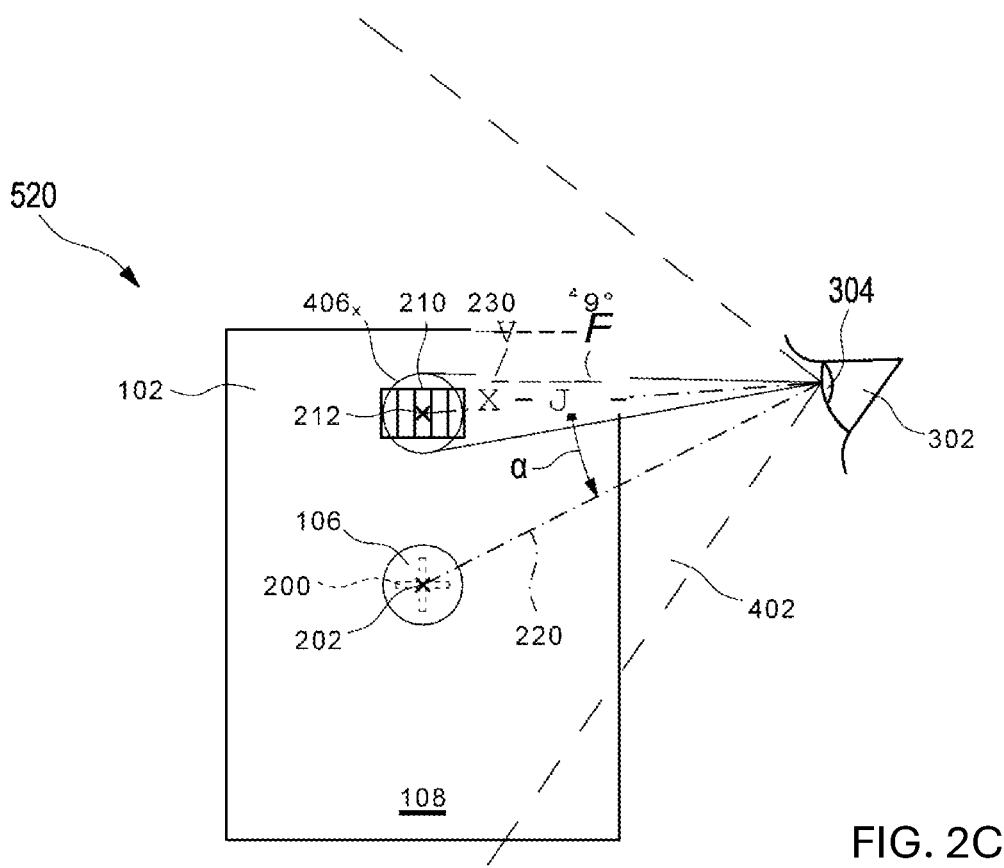

As can be seen in FIG. 2C that also illustrates the second displaying step 520, the gaze position of the eye 302 of the person 300 changed onto the visual stimulus 210 as intended as the person 300 reacted to the displaying of the visual stimulus 210. Consequently, the line of sight 410 also changed in a manner that it now intersects with visual stimulus 210.

The at least one visual stimulus 210 is continuously displayed during the second displaying step 520 and the second spatial location of the visual stimulus 210 may be fixed. The second spatial location of the visual stimulus 210 may be defined by a certain eccentricity level and a certain spatial orientation of the center 212 of the visual stimulus 210 with regard to the center 202 of the visual fixation mark 200.

During the displaying on the screen 102, the appearance of the visual stimulus 210 is time-varying. For this, a parameter attributed to the appearance of the visual stimulus 210 is varied between a first value and a second value. The parameter may be varied in a continuous manner or even a monotonous manner. The parameter varied to determine the visual acuity is here a spatial frequency of the visual stimulus 210, as can be seen by a comparison of FIG. 2B and FIG. 2C. Alternatively, the parameter may be a contrast, in particular for determining the contrast sensitivity; a color, in particular for determining the color vision; or a time-related frequency, in particular for determining a time-related sensitivity. It is further possible, that a plurality of parameters attributed to the appearance is varied between a first value and a second value. Also, the varying of the plurality of parameters may be in a continuous manner or in a monotonous manner.

According to a generating step 520 according to step c) of the method 500 for determining the visual performance within the visual field 400, 402 of the eye 302 of the person 300, the eye movement is tracked using the eye-tracking device 104. Therefore, a time variance of the gaze position or a time variance of the line of sight 410 may be recorded.

For the parameter attributed to the appearance a first threshold may be determined at which the eye movement in the eye 302 of the person 300 is tracked for the first time and a second threshold value may be determined at which the eye movement in the eye 302 of the person 300 is tracked for the last time.

Additionally, also a pupil size of a pupil 304 of the eye 302 of the person 300 is recorded by using the eye tracking device 104. By doing so, a time-variance of the pupil size may be recorded.

Figure 3:
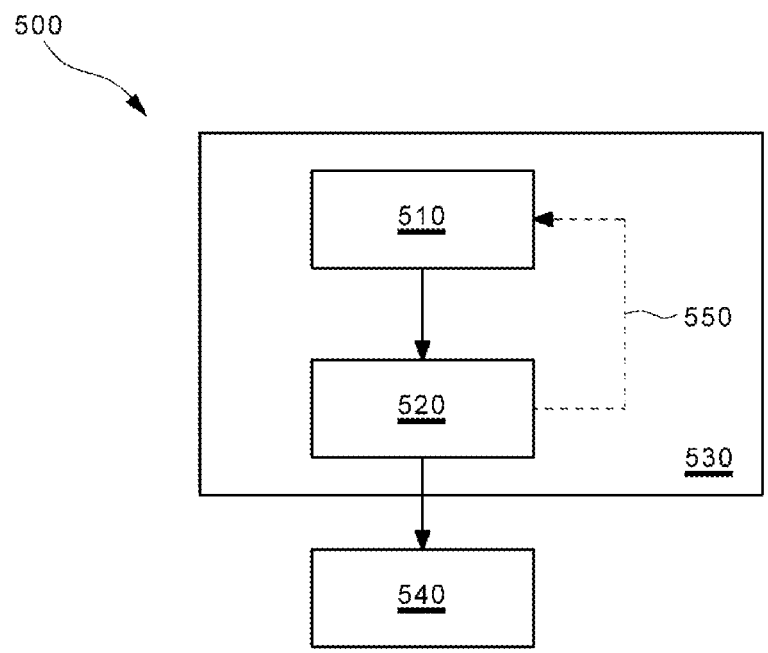
FIG. 3 illustrates a schematic view of an exemplary sequence of the method step.

FIG. 3 gives an overview of the sequence of the steps according to the method 500 for determining the visual performance of the eye 302 of the person 300. A generating step 530 according to step c) is performed during the first displaying step 510 according to step a) and the second displaying step 520 according to b). Herein, the first displaying step 510 is performed before the second displaying step 520. A measurement cycle 550 may comprise a sequence of the first displaying step 510, the second displaying step 520 and the generating step 530; however, the first displaying step 510 may not, necessarily, be comprised by the measurement cycle 550. To determine the visual performance for further points in the visual field 400, 402 the visual stimulus 210 is displayed at different second spatial locations during the second displaying step 520 during a plurality of measurement cycles 550. The method 500 for determining the visual performance within the visual field 400, 402 further comprises a determining step 550 according to step d) of the method 500.

During the second displaying step 520 the visual stimulus 210 may be displayed for a maximum of a predetermined time. In case the eye movement may not be elicited within the predetermined time, the second displaying step 520 may then be repeated using a visual stimulus 210 having a different parameter and/or spatial location.

Displaying the at least one visual stimulus 210 during the second displaying step 520 may be stopped, when the at least one eye movement elicited by the visual stimulus 210 has been tracked. In this case, the second displaying step 520 may then be considered as being completed.

The second displaying step 520 may, further, be repeated when a visual disturbance may be detected, which affects the ability of the eye 302 of the person 300 to observe the visual stimulus 210. Such a disturbance may be a blink of the eye 302 of the person 300, a gaze position of the eye 302 outside of the screen 102 displaying the visual stimulus 210, a vergence angle between both eyes of the person 300 showing that the person 300 is not focusing on the screen 102, or a pupil size showing that the person 300 is not focusing on the screen 102.

According to FIGS. 2A, 2B, and 2C, the second spatial location of the visual stimulus 210 is with regard to the fixation mark 200 at a top spatial location for determining the visual performance of an inferior visual field. Alternatively, it may be at a bottom spatial location for determining the visual performance of a superior visual field, a left spatial location for determining the visual performance of a nasal visual or a temporal visual field, respectively, or a right spatial location for determining the visual performance of the temporal visual field or the nasal visual field, respectively. To determine the peripheral field of view 402 in the inferior visual field, the superior visual, the nasal visual and the temporal visual field an outcome may be generated from four measurement cycles 550 in which the visual stimulus 210 is displayed at the top spatial location, the bottom spatial location, the left spatial location and the right spatial location. On the other hand, the visual fixation mark 200 may be displayed at the same spatial location during the first displaying step 510 of each measurement cycle 550.

The second spatial location at which the visual stimulus 210 may be displayed is determined randomly by an algorithm. Alternatively or in addition, the second spatial location at which a subsequent visual stimulus 210 in a subsequent measurement cycle 550 is displayed may be determined by considering an outcome of a particular visual stimulus 210 determined in a particular measurement cycle 550 as performed before the subsequent measurement cycle 550. For doing so, a psychometric procedure may be used that may be selected from a staircase procedure or a Bayesian method.

To determine the visual attention a reaction time may be recorded. The reaction time may be a time difference between displaying the visual stimulus 210 on the screen 102 and an occurrence of the at least one eye movement elicited by the visual stimulus 210. This measurement may, further, include emitting an attention stimulus configured to direct a focus of the person 300 to an upcoming displaying of the visual stimulus 210. The attention stimulus may be a visual signal, an audio signal, and/or a tactile signal.

After each measurement cycle 550 an outcome may be generated including the tracking data generated by the eye tracking device 104 and the second spatial location at which the visual stimulus 210 is displayed on the screen 102. Additionally, the outcome may include the visual stimulus 210, the tracking data generated by the eye tracking device 104, a flag, the first threshold, the second threshold, the pupil size, the reaction time, and/or the attention stimulus.

The flag can be used to categorize the visual stimulus 210 displayed during step b) as "seen", when the eye movement elicited by the visual stimulus 210 has been tracked during displaying the visual stimulus 210. The flag can, further, be used to categorize the visual stimulus 210 displayed during step b) as "not seen", when the eye movement elicited by the visual stimulus 210 has not been tracked during displaying the visual stimulus 210.

The outcome can be analyzed to determine the visual performance by using at least one processing device of the apparatus 100 for the points in the visual field 400, 402 that correspond to the second spatial locations at which the visual stimulus 210 has been displayed. To determine the at least one visual performance of a specific point in the visual field during the determining step 550 an assignment rule can be applied. The assignment rule may consider the first spatial location of the visual fixation mark 200 and the second spatial location of the visual stimulus 210. The assignment rule may, further, consider a distance between the eye 302 of the person 300 and the visual stimulus 210 and/or the visual fixation mark 200.

Additionally, an attention level of the person 300 may be determined by evaluating a time-related difference in the reaction times between the particular measurement cycle 550 and the measurement cycle 550 that was performed a given time interval later than the particular measurement cycle 550. In this analysis, a plurality of reaction times of the particular measurement cycle 550 and a plurality of reaction times of the subsequent measurement cycle 550 may be correlated, for example by calculating a mean-value, determining a maximal value, or determining a minimal value.

Figure 4:
FIG. 4 illustrates an exemplary system comprising the apparatus and a remote apparatus for determining at least one visual performance of at least one eye of a person.

As shown in FIG. 4, the apparatus 100 for determining the visual performance may transfer the outcome to a remote apparatus 110 for determining the visual performance within the visual field 400, 402 of the eye 302 of the person 300. Therefore, the apparatus 100 for determining the visual performance within the visual field 400, 402 and the remote apparatus 110 for determining the visual performance within the visual field 400, 402 of the eye 302 of the person 300 each comprise a connecting interface. The connecting interface may be a network interface controller and/or a transmitter.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

LIST OF REFERENCE SIGNS

100 apparatus for determining at least one visual performance of at least one eye of a person
102 screen
104 eye-tracking device
106 center area
108 surrounding area
110 remote apparatus for determining at least one visual performance of at least one eye of a person
200 visual fixation mark
202 center
210 visual stimulus
212 center
220 first connecting line
230 second connecting line
300 person
302 eye
304 pupil
400 central field of view
402 peripheral field of view
404 third connecting line
406 outer perimeter
410 line of sight
500 method for determining at least one visual performance of at least one eye of a person
510 first displaying step
520 second displaying step
530 generating step
540 determining step
550 measurement cycle
α angle
β angle

The invention claimed is:

1. A computer-implemented method for determining at least one visual performance of at least one eye of a person, the method comprising at least the following steps:
   a) displaying on a screen to the at least one eye of a person at least one visual fixation mark configured to attract a visual perception of the person by directing a line of sight of the at least one eye of the person towards the visual fixation mark;

b) subsequently displaying on the screen to the at least one eye of the person at least one visual stimulus configured to elicit at least one eye movement in the at least one eye of the person towards the at least one visual stimulus;

c) generating tracking data about the at least one eye movement of the at least one eye of the person by using at least one eye-tracking device; and d) determining the at least one visual performance from the tracking data by using at least one processing device, wherein the at least one visual performance of the at least one eye of the person is determined for at least one point in a visual field of the person by using a first spatial location of the at least one visual fixation mark and a second spatial location of the at least one visual stimulus, and wherein an attention level of the person is determined by evaluating a time-related difference in reaction times between at least one particular measurement cycle and at least one subsequent measurement cycle.

2. The method according to claim 1, wherein a measurement cycle comprises at least step b) and step c), and wherein at least two measurement cycles are repeated for determining a plurality of points in the visual field, optionally with a differing second spatial location of the at least one visual stimulus.

3. The method according to claim 1, wherein the at least one visual performance is determined for a particular point in the visual field by assigning the second spatial location of the at least one visual stimulus to the particular point using an assignment rule, wherein the assignment rule defines a relationship between the second spatial location of the at least one visual stimulus on the screen and the particular point in the visual field, and wherein the assignment rule is maintained during the at least two measurement cycles.

4. The method according to claim 1, wherein the at least one visual fixation mark is displayed in a center area of the screen, wherein the at least one visual stimulus is displayed in a surrounding area, wherein the center area is completely enclosed by a surrounding area, wherein an angle α is given between a first connecting line and a second connecting line, wherein the first connecting line connects a center of the at least one visual fixation mark and at least one reference position in the at least one eye of the person, wherein the second connecting line connects a center of the at least one visual stimulus and the at least one reference position in the at least one eye of the person, and wherein a is larger than at least one of: 2°; 3°; 4°; 5°; 6°; 7°; or 8°.

5. The method according to claim 1, wherein the visual performance of the at least one eye of the person is selected from at least one of:
a contrast sensitivity;
a visual acuity;
a color vision;
a time-related sensitivity; or
a visual attention.

6. The method according to claim 5, wherein an appearance of the at least one visual stimulus is displayed in a time-varying manner on the screen, wherein at least one parameter attributed to the appearance of the at least one visual stimulus is varied between a first value and a second value, and wherein the at least one parameter is selected from at least one of:

a contrast, in particular for determining the contrast sensitivity;
a spatial frequency, in particular for determining the visual acuity;
a color, in particular for determining the color vision; or
a time-related frequency, in particular for determining a time-related sensitivity.

7. The method according to claim 1, wherein the second spatial location of the at least one visual stimulus is placed with regard to the first spatial location of the at least one visual fixation mark at at least one of:
a top spatial location for determining the at least one visual performance of an inferior visual field;
a bottom spatial location for determining the at least one visual performance of a superior visual field;
a left spatial location for determining the at least one visual performance of a nasal visual field or a temporal visual field, respectively; or
a right spatial location for determining the at least one visual performance of a temporal visual field or a nasal visual field, respectively.

8. The method according to claim 1, wherein step b) is repeated when at least one visual disturbance which affects the ability of the at least one eye of a person to observe the visual stimulus is detected, particularly wherein the at least one visual disturbance is selected from at least one of:
a blink of the at least one eye of the person;
a gaze position of the at least one eye of the person outside of the screen displaying the visual stimulus;
a vergence angle between both eyes of the person showing that the person is not focusing on the screen; or
a pupil size showing that the person is not focusing on the screen.

9. The method according to claim 1, wherein a reaction time is determined during step b) for determining the visual attention, wherein the reaction time is a time difference between displaying the at least one visual stimulus on the screen and an occurrence of the at least one eye movement, in particular the occurrence of the at least one eye movement as elicited by the at least one visual stimulus.

10. The method according to claim 1, wherein step b) comprises emitting an attention stimulus configured to direct a focus of the person to an upcoming displaying of the at least one visual stimulus, optionally wherein the attention stimulus is selected from at least one of:
a visual signal;
an audio signal; or
a tactile signal.

11. The method according to claim 1, wherein the second spatial location at which at least one subsequent visual stimulus in at least one subsequent measurement cycle is displayed is determined by considering at least one particular visual stimulus by using a psychometric procedure.

12. A non-transitory computer readable storage medium comprising instructions which, when the program is executed by a computer, cause the computer to carry out a computer-implemented method for determining at least one visual performance of at least one eye of a person, wherein the method comprises at least the following steps:
a) displaying on a screen to the at least one eye of a person at least one visual fixation mark configured to attract a visual perception of the person by directing a line of sight of the at least one eye of the person towards the visual fixation mark;
b) subsequently displaying on the screen to the at least one eye of the person at least one visual stimulus configured to elicit at least one eye movement in the at least one eye of the person towards the at least one visual stimulus;

c) generating tracking data about the at least one eye movement of the at least one eye of the person by using at least one eye-tracking device; and d) determining the at least one visual performance from the tracking data by using at least one processing device, wherein the at least one visual performance of the at least one eye of the person is determined for at least one point in a visual field of the person by using a first spatial location of the at least one visual fixation mark and a second spatial location of the at least one visual stimulus, and wherein an attention level of the person is determined by evaluating a time-related difference in reaction times between at least one particular measurement cycle and at least one subsequent measurement cycle.

13. An apparatus for determining at least one visual performance of at least one eye of a person, the apparatus comprising:

at least one screen configured for displaying to the at least one eye of a person at least one visual fixation mark configured to attract a visual perception of the person by directing a line of sight of the at least one eye of the person towards the visual fixation mark; and subsequently at least one visual stimulus configured to elicit at least one eye movement in the at least one eye of the person;

at least one eye-tracking device configured for generating tracking data about the at least one eye movement of the at least one eye of the person moving towards the at least one visual stimulus;

at least one processing device determining the at least one visual performance from the tracking data, wherein the at least one processing device is configured for determining the at least one visual performance of the at least one eye of the person for at least one point in a visual field of the person by using a first spatial location of the at least one visual fixation mark and a second spatial location of the at least one visual stimulus, and wherein an attention level of the person is determined by evaluating a time-related difference in reaction times between at least one particular measurement cycle and at least one subsequent measurement cycle.

* * * * *

UNITED STATES PATENT AND TRADEMARK OFFICE
CERTIFICATE OF CORRECTION

| | | |
|---|---|---|
| PATENT NO. | : 12,178,510 B2 | Page 1 of 1 |
| APPLICATION NO. | : 18/642291 | |
| DATED | : December 31, 2024 | |
| INVENTOR(S) | : Siegfried Wahl, Peter Essig and Yannick Sauer | |

It is certified that error appears in the above-identified patent and that said Letters Patent is hereby corrected as shown below:

In the Specification

In Column 1, Line 63: change "Bonnch" to -- Bonneh --

In Column 9, Line 5: change "be" to -- by --

In Column 17, Line 59: change "or a" to -- a --

In Column 26, Line 61: change "or a" to -- a --

In the Claims

In Column 33, Line 51, Claim 4: change "a" to -- α --

Signed and Sealed this
Fourth Day of February, 2025

Coke Morgan Stewart
*Acting Director of the United States Patent and Trademark Office*